US006602667B1

(12) United States Patent
Walker et al.

(10) Patent No.: US 6,602,667 B1
(45) Date of Patent: *Aug. 5, 2003

(54) INFLAMMATION-ASSOCIATED POLYNUCLEOTIDES

(75) Inventors: Michael G. Walker, Sunnyvale, CA (US); Wayne Volkmuth, Calabasas, CA (US); Tod M. Klingler, San Carlos, CA (US)

(73) Assignee: Incyte Corporation, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/855,323

(22) Filed: May 14, 2001

Related U.S. Application Data

(63) Continuation-in-part of application No. 09/195,292, filed on Nov. 18, 1998, now abandoned.

(51) Int. Cl.$^7$ .................. C12Q 1/68; C12P 21/06; C07H 21/04; C12N 15/00; C12N 15/09; C12N 15/63; C12N 15/70; C12N 15/74
(52) U.S. Cl. .................. 435/6; 435/69.1; 435/320.1; 536/23.1; 536/24.3; 536/24.31
(58) Field of Search ................ 536/23.1, 24.3, 536/24.31; 435/6, 69.1, 320.1

(56) References Cited

U.S. PATENT DOCUMENTS

| | | | |
|---|---|---|---|
| 5,876,946 A | | 3/1999 | Burbaum et al. |
| 6,140,488 A | * | 10/2000 | Zhang et al. ............ 536/23.5 |

OTHER PUBLICATIONS

Vavvas, D. et al., "Identification of Nore1 as a Potential Ras Effector", J. Biol. Chem., vol. 273, pp. 5439–5442 (1998).*
Accession No. BC004270, "Homo sapiens, similar to protein interacting with guanine nucleotide exchange factor", Jul. 12, 2001.*
Accession No. BC007203, "Homo sapiens, hypothetical protein MGC10823", Jul. 12, 2001.*
Accession No. AF002251, "Rattus norvegicus Maxp1 mRNA", Oct. 2, 1997.*
Accession No. AR118132, "US patent 6,140,488; ras–binding protein (PRE1)", May 16, 2001.*
Accession No. AF053959, "Mus musculus putative ras effector Nore1 mRNA", Mar. 31, 1998.*
Adra, C.H., et al., *LAPTM5: A Novel Lysosomal–Associated Multispanning Membrane Protein Preferentially Expressed in Hematopoietic Cells*, Genomics, 35:328–337, (1996).
Al–Mokdad, M. et al, *Differential Production of Chemokines by Phagocytosing Rat Neutrophils and Macrophages*, Inflammation, 22(2):145–159, (1998).
Anderson, K.L., et al., *Myeloid Development is Selectively Disrupted in PU.1 Null Mice*, Blood, 91(10):3702–3710, (May 15 1998).
Arunachalam, B., et al., *Intracellular Formation and Cell Surface Expression of a Complex of an Intact Lysosomal Protein an dMHC Class II Molecules*, J Immunol, 160(12):5797–806, (1998).
Asman, B., et al., *Priming of neutrophils with tumor necrosis factor–alpha measured as Fc gamma receptor–mediated respiratory burst correlates with increased complement receptor 3 membrane density*, Int J Clin Lab Res, 26(4):236–9, (1996).
Bleul, C.C., et al., *The lymphocyte chemoattractant SDF–1 is a ligand for LESTR/fusin and blocks HIV–1 entry*, Nature, 382:829–833, (Aug. 29 1996).
Byrum, R.S., et al., *Role of the 5–Lipoxygenase–activating Protein (FLAP) in Murine Acute Inflammatory Responses*, J Exp Med, 185(6):1065–75, (1997).
Caroll, G., et al., *Antagonism of the IL–6 cytokine subfamily—a potential strategy for more effective therapy in rheumatoid arthritis*, Inflamm. Res., 47(1):1–7, (1998).
De Vries, L., et al., *RGS–GAIP, a GTPase–activating Protein for Gα: Heterotrimeric G Proteins, Is Located on Clathrin–coated Vesicles*, Molecular Biology of the Cell, 9(5):1123–34, (May 1998).
De Vries, L., et al., *GaIP, a protein that specifically interacts with the trimeric G protein Gα$_{13}$, is a member of a protein family with a highly conserved core domain*, Proc Natl Acad Sci USA, 92(25):11916–20, (Dec 1995).
Denzin, L.K., et al., *HLA–DM induces CLIP dissociatio from MHC class II alpha..*, Cell, 82(1):155–65, (1995).
Dorseiul, O.L., et al., *The Rac Target NADPH Oxidase p67$^{phox}$ Interacts Preferentially with Rac2 Rather Than Rac1*, Journal of Biological Chemistry, 271(1):83–8, (1996).
Ericson, S.G., et al., *Interleukin–6 Production by Human Neutrophils After Fc–Receptor Cross–Linking or Exposure to Granulocyte Colony–Stimulating Factor*, Blood, 91(6):2099–2107, (Mar. 15, 1998).
Faris, S.L., et al., *Phagocyte NADPH Oxidase p67–phox Possesses a Novel Carboxylterminal Binding Site for the GTPases Rac2 and Cdc42$^1$*, Biochem. Biophys. Res Commun, 247(2):271–6, (1998).
Frederick, M.J., et al., *Characterizatio of the Mr 65,000 Lymphokine–activated Killer Proteins Phosphorylated after Tumor Targeted Binding: Evidence That pp65a and pp65b Are Phosphorylated Forms of L–Plastin*, Cancer Research, 56(1):138–144, (Jan. 1, 1996).
Greer, S.F., et al., *Major Histocompatibility Class II–mediated Signal Transduction Is Regulated by the Protein–tyrosine Phosphatase CD45*, Journal of Biological Chemistry, 273(19):11970–11979, (May 1998).

(List continued on next page.)

Primary Examiner—Kenneth R. Horlick
Assistant Examiner—Teresa Strzelecka
(74) Attorney, Agent, or Firm—Incyte Corporation

(57) ABSTRACT

The invention provides compositions and novel polynucleotides and proteins that co-express with known marker genes for inflammatory disorders. The invention also provides expression vectors, host cells, proteins encoded by the polynucleotides and antibodies which specifically bind the proteins. The invention also provides methods for the diagnosis, prognosis, evaluation of therapies and treatment of inflammatory disorders.

15 Claims, No Drawings

OTHER PUBLICATIONS

Hendricks–Taylor, L.R., et al., *SLP–76 is a Substrate of the High Affinity IgE Receptor–stimulated Protein Tyrosine Kinases in Rat Basophilic Leukemia Cells*, Journal of Biological Chemistry, 272(2):1363–1367, (Jan. 10, 1997).

Hui, W., et al., *Detection of oncostatin M in synovial fluid from patients with rheumatoid arthritis*, Annals of the Rheumatic Diseases, 56(3):184–187, (1997).

Jackman, J.K., et al., *Molecular Cloning of SLP–76, a 76–kDa Tyrosine Phosphoprotein Associated with Grb2 in T Cells*, Journal of Biological Chemistry, 270(13):7029–7032, (1995).

Jiang, Z., et al., *Structure, Organization, and Chromosomal Mapping of the Gene Encoding Macrosialin, a Macrophage–Restricted Protein*, Genomics, 50(2):199–205, (1998).

Jones, S.L., et al., *FcαRII–mediated Adhesion and Phagocytosis Induce L–Plastin Phosphorylation in Human Neutrophils*, Journal Biological Chemistry, 271(24):14623–14630, (1996).

Larsen, J.S., et al., *Antileukotriene therapy for asthma*, Am J Health–Syst Pharm, 53(23):2821–30, (1996).

Levy, S., et al., *CD81 (TAPA–1): A Molecule Involved in Signal Transduction and Cell Adhesion in the Immune System*, Annu. Rev. Immunol., 16:89–109, (1998).

Li, S., et al., *PU.1 is essential for p47$^{phox}$ promoter activity in myeloid cells*, Journal of Biological Chemistry, 272(28):17802–17809, (1997).

Loetscher, M., et al., *Cloning of a Human seven–transmembrane Domain Receptor, LESTR, that is highly expressed in leukocytes*, Journal of Biological Chemistsry, 269(1):232–237, (1994).

Lowell, C.A., et al., *Resistance to endotoxic shock and reduced neutrophil migration in mice deficient for the Src–family kinases Hck and Fgr*, Proc Natl Acad Sci USA, 95(13):7580–7584, (Jun. 1998).

Luster, A.D., et al., *Molecular and Biochemical Characterization of a Novel α–interferon–inducible protein*, Journal of Biological Chemistry, 263(24):12036–12043, (1988).

Maecker, H.T., et al., *The tetraspanin superfamily: molecular facilators*, Faseb J, 11(6):428–42, (1997).

Meischl, C., et al., *The molecular basis of chronic granulomatous disease*, Springer Semin Immunopathol, 19:417–434, (1998).

Mizuno, K., et al., *Hematopoietic Cell Phosphatase, SHP–1, Is Constitutively Associated with the SH2 Domain–containing Leukocyte Protein, SLP–76, in B Cells*, J Exp Med, 184(2):457–463, (1996).

Modur, V., et al., *Oncostatin M is a Proinflammatory Mediator*, J. Clin Invest, 100(1):158–168, (Jul. 1997).

Mollinedo, Faustino, et al., *Physiological activation of human neutrophils down–regulates CD53 cell surface antigen*, J Leukoc Biol, 63(6):699–706, (1998).

Pandey, A., et al., *Characterization of a Novel Src–like Adapter Protein That Associates with the Eck Receptor Tyrosine Kinase*, Journal of Biological Chemistry, 270(33):19201–19204, (1995).

Pandey, A., et al., *Role of B61, the Ligand for the Eck Receptor Tyrosine Kinase, in TNF–α–Induced Angiogenesis*, Science, 268(5210):567–9, (1995).

Romette, J., et al., *Inflammatory syndrome and plasma protein changes*, Path Biol (Paris), 34(9):1006–12, (1986).

Rouard, H., et al., Abstract, *Fc receptors as targets for immunotherapy*, Int Rev Immunol, 16(1–2):147–85, (1997).

Samaridis, J., et al., *Cloning of novel immunoglobulin superfamily receptors expressed on human myeloid and lymphoid cells: structural evidence for new stimulatory and inhibitory pathways*, Eur J Immunol, 27(3):660–5, (1997).

Shibata, M., et al., *Characterizatin of a 64–kd protein phosphorylated during chemotactic activation with IL–8 and fMLP of human polymorphonuclear with IL–8 and fMLP of human polymorphonuclear leukocytes. I Phosphorylation of a 64–kd protein and a other proteins*, Journal of Leukocyte Biology, 54(1):1–9, (1993).

Shibata, M., et al., *Characterizationo f a 64–kd protein phosphorylated during chemotactic actiation with Il–8 and fMLP of human polymorphonuclear leukocytes. II. Purification and amino acid analysis of phosphorylated 64–kd protein*, Journal of Leukocyte Biology, 54(1):10–6, (1993).

Su, G.H., et al., *The Ets Protein Spi–B is Expressed Exclusively in B Cells and T Cells During Development*, J Exp Med, 184(1):203–14, (1996).

Suzuki, K., et al., *Molecular cloning of a novel actin–binding protein, p57, with a WD repeat and a leucine zipper motif*, FEBS Letter, 364(3):283–8, (1995).

Suzuki, S., et al., *PU.1 as an essential activator for the expression of gp91$^{phox}$ gene in human peripheral neutrophils, monocytes, and B lymphocytes*, Proc Natl Acid Sci USA, 95(11):6085–6090, (May 1998).

Tan, R., et al., *The role of antileukotrienes in asthma management*, Current Opinion in Pulmonary Medicine, 4:25–30, (1998).

Wardenburg, J.B., et al., *Phosphorylation of SLP–76 by the ZAP–70 Protein–tyrosine Kinase is required for T–cell Receptor Function*, Journal of Biological Chemistry, 271(33):19641–44, (1996).

Zu, Y., et al., *Characterization of Interleukin 2 Stimulated 65–kilodalton Phosphoprotein in Human T Cells*, Biochemistry, 29:1055–1062, (1990).

Walker and Volkmuth, Prediction of gene function by genome–scale expression analysis: prostate–associated genes. Genome Res 9:1198–1203 (1999).

Tamm et al., The IgG Binding Site of Human FcγRIIIB Receptor Involves CC' and FG Loops of the Membrane–proximal Domain, The Journal fo Biological chemistry, vol. 271, pp. 3659–3666, 1996.

Fröhlich, et al., The Fcγ Receptor–Mediated Respiratory Burst of Rolling Neutrophils to Cytokine–Activated, Immune Complex–Bearing Endothelial Cells Depends on L–Selectin But Not on E–Selectin, Blood, vol. 91, No. 7, pp. 2558–2564, 1998.

Pandey, et al., characterization of a Novel Src–like Adapter Protein That Associates with the Eck Receptor Tyrosine Kinase,JBC 240:1924–19200, 1995.

Luster, et al., Molecular and Biochemical Characterization of a Novel γ–Interferon–inducible Protein, The Journal of Biological Chemistry, vol. 263, pp. 12036–12443, 1988.

Ratnam, S., and Mookerjea, S., The Regulation of Superoxide Generation and Nitric Oxide Synthesis by C–reactive Protein, Blackwell Science Ltd., vol. 94(4), pp. 560–568, 1998.

Breit and Penny, The Role of $\alpha_1$ Protease Inhibitor ($\alpha_1$ Antitrypsin) in the Regulation of Immunologic and Inflammatory Reactions, Aust. N.Z.J. Med., vol. 10, pp. 449–453, 1980.

Alberts, et al., Molecular Biology of the Cell, Garland Publishing, p. 1214, 1994.

Brum et al., Role of the 5-Lipoxygenase-activating Protein (FLAP) in Murine Acute Inflammatory Responses, J. J Exp Med, vol. 185, pp. 1065–1075, 1997.

Lowell and Berton, Resistance to Resistance to Endotoxic Shock and Reduced Neutrophil Migration in Mice Deficient for the Src-family Kinases Hck and Fgr, Proc, Natl, Acad, Sci. USA, vol. 95, pp. 7580–7584, 1998.

Marsh et al., Lymphocytes Produce IL-1β in Response to Fcγ Receptor Cross-Linking: Effects on Parenchymal Cell IL-8 Release, J. Immunol., v. 160, p. 3942 (1998).

Pandey et al., Role of B61, The Ligand forthe Eck Receptor Tyrosine Kinase, in TNF-Alpha-Induced Angiogenesis, Science, Apr 28,268 (5210): 567–9, 1995.

Arnuachalam et al., Intracellular Formation and Cell Surface Expression of a Complex of an Intact Lysosomal Protein and MHC Class II Molecules, The American Association of Immunologists, 1998.

Schuelke et al., Cloning of the Human Mitochondrial 51 kDa Subunit (NDUFV1) Reveals a 100% Antisense Homology of its 3'UTR of the Gamma-Interferon Inducible Protein (IP-30) precursor: Is This a Link Between Mitochondrial Myopathy and Inflammation?, Biochem Biophys Res Commun 1998.

* cited by examiner

US 6,602,667 B1

INFLAMMATION-ASSOCIATED POLYNUCLEOTIDES

This application is a continuation-in-part of U.S. Ser. No. 09/195,292, filed Nov. 18, 1998 now abandoned.

FIELD OF THE INVENTION

The invention relates to eleven isolated polynucleotides and their encoded proteins that are highly co-expressed with genes known to be diagnostic markers of inflammation and useful for diagnosis, prognosis, treatment of inflammatory disorders.

BACKGROUND OF THE INVENTION

Inflammation is the body's immediate, general response to wounding or infection by a pathogen. There are many complex phenomena that occur during an inflammation response. Initiation of the complement cascade, leukocyte recruitment and leukocyte activation are three key events. In the complement cascade a set of serum proteins collectively called complement non-specifically coat foreign matter. The coating proceeds in a cascade of steps using particular subsets of factors called complement components. The coated particles are then phagocytosed by macrophages or neutrophils recruited to the inflammation site. Leukocyte recruitment of monocytes and neutrophils is mediated by cytokines, which are proteins secreted by tissue at the inflammation site. Interleukin-8 (IL-8) is the primary chemoattractant cytokine responsible for recruitment in the initial stage of inflammation. In response to IL-8, monocytes and neutrophils are activated. An immediate response to activation is the expression of L-selectin and the integrins. L-selectin is a surface molecule that facilitates leukocyte binding (with relatively low affinity) to the endothelial cells lining blood vessels in the vicinity of the inflammation site. The integrins, also cell surface molecules, have stronger binding and mediate the actual extravasation of leukoctyes from the blood vessel. Upon reaching the site of inflammation, receptors to the complement factors coating foreign particles are expressed on the leukocytes leading to phagocytosis and enzymatic degradation.

Many genes that participate in and regulate the inflammation response are known, but many remain to be identified. Identification of currently unknown genes will provide new diagnostic markers and therapeutic targets for control of the inflammation response and treatment of inflammatory disorders.

The present invention provides new compositions that are highly co-expressed with genes known to be diagnostic of inflammatory disorders and useful for diagnosis, prognosis, evaluation of therapies and treatment of inflammatory disorders.

SUMMARY OF THE INVENTION

The invention provides for a plurality of polynucleotides having the nucleic acid sequences of SEQ ID NOs:1–11 or the complements thereof that are co-expressed with genes such as CD16; L-selectin; Src-like adapter protein (SLAP); IP-30; superoxidase homoenzyme subunits, p67phox, p47phox, and p40phox; alpha-1-antitrypsin (AAT); Clq-A; 5-lipoxygenase activating protein (FLAP); and SRC family tyrosine kinase (HCK) known to be highly expressed during inflammation. The invention also provides an isolated polynucleotide comprising a nucleic acid sequence selected from SEQ ID NOs:1–or the complement thereof. In different aspects, the polynucleotide is used as a surrogate marker, as a probe, in an expression vector, and in the diagnosis, prognosis, evaluation of therapies and treatment of inflammatory disorders. The invention further provides a composition comprising either a plurality of polynucleotides or a polynucleotide and a labeling moiety.

The invention provides a method for using a composition or a polynucleotide of the invention to screen a plurality of molecules and compounds to identify ligands which bind the polynucleotide(s). The molecules are selected from DNA molecules, RNA molecules, peptide nucleic acids, peptides, mimetics, ribozymes, transcription factors, enhancers, and repressors. The invention also provides a method of using a composition or a polynucleotide to purify a ligand.

The invention provides a method for using a composition or an isolated polynucleotide to detect gene expression in a sample by hybridizing the composition or polynucleotide to nucleic acids of the sample under conditions for formation of one or more hybridization complexes and detecting hybridization complex formation, wherein complex formation indicates gene expression in the sample. In one aspect, the composition or polynucleotide is attached to a substrate. In another aspect, the nucleic acids of the sample are amplified prior to hybridization. In yet another aspect, complex formation is compared with at least one standard and indicates the presence of an inflammatory disorder.

The invention provides a purified protein or a portion thereof, SEQ ID NOs:12–17, which is encoded by a polynucleotide that is co-expressed with genes that are diagnostic markers of inflammation or inflammatory disorders. The invention also provides a method for using a protein to screen a plurality of molecules to identify at least one ligand which specifically binds the protein. The molecules are selected from aptamers, DNA molecules, RNA molecules, peptide nucleic acids, peptides, mimetics, ribozymes, proteins, antibodies, agonists, antagonists, immunoglobulins, inhibitors, pharmaceutical agents or drug compounds. The invention further provides a method of using a protein to purify a ligand.

The invention provides a method of using a protein to make an antibody that specifically binds to the protein of the invention, and methods for using the antibody to diagnose or treat an inflammatory disorder. The invention further provides a composition comprising a polynucleotide, a protein, or an antibody that specifically binds a protein and a pharmaceutical carrier.

BRIEF DESCRIPTION OF THE SEQUENCE LISTING

The Sequence Listing provides exemplary polynucleotides comprising the nucleic acid sequences of SEQ ID NOs:1–11 some of which encode the proteins comprising the amino acid sequences of SEQ ID NOs:12–17. Each sequence is identified by a sequence identification number (SEQ ID NO) and by the Incyte clone number with which the sequence was first identified.

DESCRIPTION OF THE INVENTION

It must be noted that as used herein and in the appended claims, the singular forms "a", "an", and "the" include the plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Definitions

"Markers for inflammatory disorders" refers to polynucleotides, proteins, and antibodies which are useful in the diagnosis, prognosis, evaluation of therapies and treatment of inflammatory disorders. Typically, this means that the marker gene is differentially expressed in samples from subjects predisposed to, manifesting, or diagnosed with an inflammatory disorder.

"Differential expression" refers to an increased or upregulated or a decreased or downregulated expression as detected by presence, absence or at least about a two-fold change in the amount of transcribed messenger RNA or protein in a sample.

"Inflammatory disorders" specifically include, but are not limited to, the following conditions, diseases, and disorders: adult respiratory distress syndrome, allergy, anemia, asthma, atherosclerosis, bacterial infection, benign prostatic hyperplasia (BPH), cholecystitis, chronic heart failure (CHF), chronic ulcerative colitis, Crohn's disease, diabetes mellitus, emphysema, gastritis, hypereosinophilia, irritable bowel syndrome, lung cancer of complications thereof, lymphoma, meningitis, multiple sclerosis, osteoarthritis, psoriasis, rheumatoid arthritis, and toxic shock syndrome.

"Isolated or purified" refers to a polynucleotide or protein that is removed from its natural environment and that is separated from other components with which it is naturally present.

"Genes known to be highly expressed during inflammation" and used in the co-expression analysis included CD16; L-selectin; Src-like adapter protein (SLAP); IP-30; superoxidase homoenzyme subunits, p67phox, p47phox, and p40phox; alpha-1-antitrypsin (AAT); Clq-A; 5-lipoxygenase activating protein (FLAP); and SRC family tyrosine kinase (HCK).

"Polynucleotide" refers to an isolated cDNA. It can be of genomic or synthetic origin, double-stranded or single-stranded, and combined with vitamins, minerals, carbohydrates, lipids, proteins, or other nucleic acids to perform a particular activity or form a useful composition.

"Protein" refers to a purified polypeptide whether naturally occurring or synthetic.

"Sample" is used in its broadest sense. A sample containing nucleic acids can comprise a bodily fluid; an extract from a cell, chromosome, organelle, or membrane isolated from a cell; genomic DNA, RNA, or cDNA in solution or bound to a substrate; a cell; a tissue; a tissue print; and the like.

"Substrate" refers to any rigid or semi-rigid support to which polynucleotides or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

A "transcript image" is a profile of gene transcription activity in a particular tissue at a particular time.

A "variant" refers to a polynucleotide or protein whose sequence diverges from about 5% to about 30% from the nucleic acid or amino acid sequences of the Sequence Listing.

The Invention

The present invention employed "guilt by association or GBA", a method for using marker genes known to be associated with a particular condition, disease or disorder to identify surrogate markers, polynucleotides and their encoded proteins, that are similarly associated or co-expressed in the same condition, disease, or disorder (Walker and Volkmuth (1999) Prediction of gene function by genome-scale expression analysis: prostate-associated genes. Genome Res 9:1198–1203, incorporated herein by reference). In particular, the method identifies cDNAs cloned from mRNA transcripts which are active in tissues known to have been removed from subjects with inflammatory disorders. The polynucleotides are useful for diagnosis, prognosis, evaluation of therapies, and treatment of inflammatory disorders.

Guilt by association provides for the identification of polynucleotides that are expressed in a plurality of libraries. The polynucleotides represent genes of unknown function which are expressed in a specific signaling pathway, disease process, subcellular compartment, cell type, tissue, or species. The expression patterns of the genes known to be highly expressed during inflammation, CD16, L-selectin, SLAP, IP-30, p67phox, p47phox, p40phox, AAT, Clq-A; FLAP, and HCK, are compared with those of polynucleotides with unknown function to determine whether a specified co-expression probability threshold is met. Through this comparison, a subset of the polynucleotides having a high co-expression probability with the known marker genes can be identified.

The polynucleotides originate from human cDNA libraries. These polynucleotides can also be selected from a variety of sequence types including, but not limited to, expressed sequence tags (ESTs), assembled polynucleotides, full length coding regions, and 3' untranslated regions. To be considered in the co-expression analysis, the polynucleotides have been expressed in at least five cDNA libraries. In this application, GBA was applied to a total of 41,419 assembled gene bins to identify eleven novel polynucleotides.

The cDNA libraries used in the co-expression analysis were obtained from adrenal gland, biliary tract, bladder, blood cells, blood vessels, bone marrow, brain, bronchus, cartilage, chromaffin system, colon, connective tissue, cultured cells, embryonic stem cells, endocrine glands, epithelium, esophagus, fetus, ganglia, heart, hypothalamus, hemic/immune system, intestine, islets of Langerhans, kidney, larynx, liver, lung, lymph, muscles, neurons, ovary, pancreas, penis, phagocytes, pituitary, placenta, pleura, prostate, salivary glands, seminal vesicles, skeleton, spleen, stomach, testis, thymus, tongue, ureter, uterus, and the like. The number of cDNA libraries selected can range from as few as three to greater than 10,000 and preferably, the number of the cDNA libraries is greater than 500.

In a preferred embodiment, the polynucleotides are assembled from related sequences, such as sequence fragments derived from a single transcript. Assembly of the polynucleotide can be performed using sequences of various types including, but not limited to, ESTs, extension of the EST, shotgun sequences from a cloned insert, or full length cDNAs. In a most preferred embodiment, the polynucleotides are derived from human sequences that have been assembled using the algorithm disclosed in U.S. Ser. No. 9,276,534, filed Mar. 25, 1999, and used in U.S. Ser. No. 09/195,292, filed Nov. 18, 1998, both incorporated herein by reference.

Experimentally, differential expression of the polynucleotides can be evaluated by methods including, but not limited to, differential display by spatial immobilization or by gel electrophoresis, genome mismatch scanning, representational difference analysis, and transcript imaging. The results of transcript imaging for SEQ ID NOs:1, 2, 3, and 6 shows significant expression of these sequences in BPH, hypereosinophilia, lung cancer, and rheumatoid arthritis, respectively. The transcript images provided direct confirmation of the strength of co-expression analysis using known genes to identify unknown polynucleotides and their encoded proteins which are highly significantly associated with inflammatory disorders. Additionally, differential expression can be assessed by microarray technology. These methods can be used alone or in combination.

Genes known to be highly expressed during inflammation can be selected based on research in which the genes are found to be key elements of immune response pathways or on the known use of the genes as diagnostic or prognostic markers or therapeutic targets for inflammatory disorders. Preferably, the known genes are CD16, L-selectin, SLAP, IP-30, p67phox, p47phox, p40phox, AAT, Clq-A, FLAP, and HCK.

The procedure for identifying novel polynucleotides that exhibit a statistically significant co-expression pattern with known genes is as follows. First, the presence or absence of a polynucleotide in a cDNA library is defined: a polynucleotide is present in a cDNA library when at least one cDNA fragment corresponding to the polynucleotide is detected in a cDNA from that library, and a polynucleotide is absent from a library when no corresponding cDNA fragment is detected.

Second, the significance of co-expression is evaluated using a probability method to measure a due-to-chance probability of the co-expression. The probability method can be the Fisher exact test, the chi-squared test, or the kappa test. These tests and examples of their applications are well known in the art and can be found in standard statistics texts (Agresti (1990) *Categorical Data Analysis*, John Wiley & Sons, New York N.Y.; Rice (1988) *Mathematical Statistics and Data Analysis*, Duxbury Press, Pacific Grove Calif.). A Bonferroni correction (Rice, supra, p. 384) can also be applied in combination with one of the probability methods for correcting statistical results of one polynucleotide versus multiple other polynucleotides. In a preferred embodiment, the due-to-chance probability is measured by a Fisher exact test, and the threshold of the due-to-chance probability is set preferably to less than 0.001, more preferably to less than 0.00001.

For example, to determine whether two genes, A and B, have similar co-expression patterns, occurrence data vectors can be generated as illustrated in the table below. The presence of a gene occurring at least once in a library is indicated by a one, and its absence from the library, by a zero.

|  | Library 1 | Library 2 | Library 3 | . . . | Library N |
|---|---|---|---|---|---|
| Gene A | 1 | 1 | 0 | . . . | 0 |
| Gene B | 1 0 |  | 1 | . . . | 0 |

For a given pair of genes, the occurrence data in the table above can be summarized in a 2×2 contingency table. The second table (below) presents co-occurrence data for gene A and gene B in a total of 30 libraries. Both gene A and gene B occur 10 times in the libraries.

|  | Gene A Present | Gene A Absent | Total |
|---|---|---|---|
| Gene B Present | 8 | 2 | 10 |
| Gene B Absent | 2 | 18 | 20 |
| Total | 10 | 20 | 30 |

The second table summarizes and presents: 1) the number of times gene A and B are both present in a library; 2) the number of times gene A and B are both absent in a library; 3) the number of times gene A is present, and gene B is absent; and 4) the number of times gene B is present, and gene A is absent. The upper left entry is the number of times the two genes co-occur in a library, and the middle right entry is the number of times neither gene occurs in a library. The off diagonal entries are the number of times one gene occurs, and the other does not. Both A and B are present eight times and absent 18 times. Gene A is present, and gene B is absent, two times; and gene B is present, and gene A is absent, two times. The probability ("p-value") that the above association occurs due to chance as calculated using a Fisher exact test is 0.0003. Associations are generally considered significant if a p-value is less than 0.01 (Agresti, supra; Rice, supra).

This method of estimating the probability for co-expression makes several assumptions. The method assumes that the libraries are independent and are identically sampled. However, in practical situations, the selected cDNA libraries are not entirely independent, because more than one library can be obtained from a single subject or tissue. Nor are they entirely identically sampled, because different numbers of cDNAs can have been sequenced from each library. The number of cDNAs sequenced typically ranges from 5,000 to 10,000 cDNAs per library. After the Fisher exact co-expression probability is calculated for each polynucleotide versus all other assembled polynucleotides that occur, a Bonferroni correction for multiple statistical tests is applied.

Using the method of the present invention, we have identified polynucleotides, SEQ ID NOs:1–11 and their encoded proteins, SEQ ID NOs:12–17, that exhibit highly significant co-expression probability with known marker genes for inflammatory disorders. The results presented in Example VI show the direct (known gene to unknown polynucleotide) or indirect (known gene to unknown polynucleotide to a second unknown polynucleotide) associations among the novel polynucleotides and the known marker genes for inflammatory disorders. Therefore, by these associations, the novel polynucleotides are useful as surrogate markers for the co-expressed known marker genes in diagnosis, prognosis, evaluation of therapies and treatment of inflammatory disorders. Further, the proteins or peptides expressed from the novel polynucleotides are either potential therapeutics or targets for the identification and/or development of therapeutics.

In one embodiment, the present invention encompasses a composition comprising a plurality of polynucleotides having the nucleic acid sequences of SEQ ID NOs:1–11 or the complements thereof. These eleven polynucleotides are shown by the method of the present invention to have significant co-expression with known genes associated with inflammatory disorders. The invention also provides a polynucleotide, its complement, a probe comprising the polynucleotide or the complement thereof selected from SEQ ID NOs:1–11 and variants of the polynucleotides.

The polynucleotide can be used to search against the GenBank primate (pri), rodent (rod), mammalian (mam), vertebrate (vrtp), and eukaryote (eukp) databases; the encoded protein, against GenPept, SwissProt, BLOCKS (Bairoch et al. (1997) Nucleic Acids Res 25:217–221), PFAM, and other databases that contain previously identified and annotated protein sequences, motifs, and gene functions. Methods that search for primary sequence patterns with secondary structure gap penalties (Smith et al. (1992) Protein Engineering 5:35–51) as well as algorithms such as Basic Local Alignment Search Tool (BLAST; Altschul (1993) J Mol Evol 36:290–300; Altschul et al. (1990) J Mol Biol 215:403–410), BLOCKS (Henikoff and Henikoff (1991) Nucleic Acids Res 19:6565–6572), Hidden Markov Models (HMM; Eddy (1996) Cur Opin Str Biol 6:361–365; Sonnhammer et al. (1997) Proteins 28:405–420), and the like, can be used to manipulate and analyze nucleotide and amino acid sequences. These databases, algorithms and other methods are well known in the art and are described in Ausubel et al. (1997; *Short Protocols in Molecular Biology*, John Wiley & Sons, New York N.Y., unit 7.7) and in Meyers (1995; *Molecular Biology and Biotechnology*, Wiley VCH, New York N.Y., p 856–853).

Also encompassed by the invention are polynucleotides that are capable of hybridizing to SEQ ID NOs:1–11, and fragments thereof, under highly stringent conditions. Stringency can be defined by salt concentration, temperature, and other chemicals and conditions well known in the art. Conditions can be selected, for example, by varying the concentrations of salt in the prehybridization, hybridization, and wash solutions or by varying the hybridization and wash temperatures. With some substrates, the temperature can be decreased by adding a solvent such as formamide to the prehybridization and hybridization solutions.

Hybridization can be performed at low stringency, with buffers such as 5×SSC (saline sodium citrate) with 1% sodium dodecyl sulfate (SDS) at 60° C., which permits complex formation between two nucleic acid sequences that contain some mismatches. Subsequent washes are performed at higher stringency with buffers such as 0.2×SSC with 0.1% SDS at either 45° C. (medium stringency) or 68° C. (high stringency), to maintain hybridization of only those complexes that contain completely complementary sequences. Background signals can be reduced by the use of detergents such as SDS, sarcosyl, or TRITON X-100 (Sigma-Aldrich, St. Louis Mo.), and/or a blocking agent, such as salmon sperm DNA. Hybridization methods are described in detail in Ausubel (supra, units 2.8–2.11, 3.18–3.19 and 4–6–4.9) and Sambrook et al. (1989; *Molecular Cloning, A Laboratory Manual*, Cold Spring Harbor Press, Plainview N.Y.)

A polynucleotide can be extended utilizing primers and employing various PCR-based methods known in the art to detect upstream sequences such as promoters and other regulatory elements. (See, e.g., Dieffenbach and Dveksler (1995) *PCR Primer, a Laboratory Manual*, Cold Spring Harbor Press, Plainview N.Y.). Commercially available kits such as XL-PCR (Applied Biosystems, Foster City Calif.), cDNA libraries (Life Technologies, Rockville MD) or genomic libraries (Clontech, Palo Alto Calif.) and nested primers can be used to extend the sequence. For all PCR-based methods, primers can be designed using commercially available software (LASERGENE software, DNASTAR, Madison WI) or another program, to be about 15 to 30 nucleotides in length, to have a GC content of about 50%, and to form a hybridization complex at temperatures of about 68° C. to 72° C.

In another aspect of the invention, the polynucleotide can be cloned into a recombinant vector that directs the expression of the protein, or structural or functional portions thereof, in host cells. Due to the inherent degeneracy of the genetic code, other DNA sequences which encode functionally equivalent amino acid sequence can be produced and used to express the protein encoded by the polynucleotide. The nucleotide sequences of the present invention can be engineered using methods generally known in the art in order to alter the nucleotide sequences for a variety of purposes including, but not limited to, modification of the cloning, processing, and/or expression of the gene product. DNA shuffling by random fragmentation, as described in U.S. Pat. No. 5,830,721, and PCR reassembly of gene fragments and synthetic oligonucleotides can be used to engineer the nucleotide sequences. For example. oligonucleotide-mediated site-directed mutagenesis can be used to introduce mutations that create new restriction sites, alter glycosylation patterns, change codon preference, produce splice variants, and so forth.

In order to express a biologically active protein, the polynucleotide or derivatives thereof, can be inserted into an expression vector with elements for transcriptional and translational control of the inserted coding sequence in a particular host. These elements include regulatory sequences, such as enhancers, constitutive and inducible promoters, and 5' and 3' untranslated regions. Methods which are well known to those skilled in the art can he used to construct such expression vectors. These methods include in vitro recombinant DNA techniques, synthetic techniques, and in vivo genetic recombination (Ausubel, supra, unit 16).

A variety of expression vector/host cell systems can be utilized to express the polynucleotide. These include, but are not limited to, microorganisms such as bacteria transformed with recombinant bacteriophage, plasmid, or cosmid expression vectors; yeast transformed with yeast expression vectors; insect cell systems infected with baculovirus vectors; plant cell systems transformed with viral or bacterial expression vectors; or animal cell systems. For long term production of recombinant proteins in mammalian systems, stable expression in cell lines is preferred. For example, the polynucleotide can be transformed into cell lines using expression vectors which can contain viral origins of replication and/or endogenous expression elements and a selectable or visible marker gene on the same or on a separate vector. The invention is not to be limited by the vector or host cell employed.

In general, host cells that contain the polynucleotide and that express the protein can be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip-based technologies for the detection and/or quantification of nucleic acid or amino acid sequences. Immunological methods for detecting and measuring the expression of the protein using either specific polyclonal or monoclonal antibodies are known in the art. Examples of such techniques include enzyme-linked immunosorbent assays (ELISAs), radioimmunoassays (RIAs), and fluorescence activated cell sorting (FACS).

Host cells transformed with the polynucleotide can be cultured under conditions for the expression and recovery of the protein from cell culture. The protein produced by a transgenic cell can be secreted or retained intracellularly depending on the sequence and/or the vector used. As will be understood by those of skill in the art, expression vectors containing the polynucleotide can be designed to contain signal sequences which direct secretion of the protein through a prokaryotic cell wall or eukaryotic cell membrane.

In addition, a host cell strain can be chosen for its ability to modulate expression of the inserted sequences or to process the expressed protein in the desired fashion. Such modifications of the protein include, but are not limited to, acetylation, carboxylation, glycosylation, phosphorylation, lipidation, and acylation. Post-translational processing which cleaves a "prepro" form of the protein can also be used to specify protein targeting, folding, and/or activity.

Different host cells which have specific cellular machinery and characteristic mechanisms for post-translational activities (e.g., CHO, HeLa, MDCK, HEK293, and W138) are available from the ATCC (Manassas Va.) and can be chosen to ensure the correct modification and processing of the expressed protein.

In another embodiment of the invention, natural, modified, or recombinant polynucleotides are ligated to a heterologous sequence resulting in translation of a fusion protein containing heterologous protein moieties in any of the aforementioned host systems. Such heterologous protein moieties facilitate purification of fusion proteins using commercially available affinity matrices. Such moieties include, but are not limited to, glutathione S-transferase, maltose binding protein, thioredoxin, calmodulin binding peptide, 6-His, FLAG, c-myc, hemaglutinin, and monoclonal antibody epitopes.

In another embodiment, the polynucleotides, wholly or in part, are synthesized using chemical or enzymatic methods well known in the art (Caruthers et al. (1980) Nucl Acids Symp Ser (7) 215–233; Ausubel, supra, units 10.4 and 10.16). Peptide synthesis can be performed using various solid-phase techniques (Roberge et al. (1995) Science 269:202–204), and machines such as the ABI 431A peptide synthesizer (Applied Biosystems) can be used to automate synthesis. If desired, the amino acid sequence can be altered during synthesis to produce a more stable variant for therapeutic use.

Screening, Diagnostics and Therapeutics

The polynucleotides can be used as surrogate markers in diagnosis, prognosis, evaluation of therapies and treatment of inflammatory disorders including but not limited to adult respiratory distress syndrome, allergy, anemia, asthma, atherosclerosis, bacterial infection, benign prostatic hyperplasia (BPH), cholecystitis, chronic heart failure (CHF), chronic ulcerative colitis, Crohn's disease, diabetes mellitus, emphysema, gastritis, hypereosinophilia, irritable bowel syndrome, lung cancer of complications thereof, lymphoma, meningitis, multiple sclerosis, osteoarthritis, psoriasis, rheumatoid arthritis, and toxic shock syndrome.

The polynucleotide can be used to screen a plurality or library of molecules and compounds for specific binding affinity. The assay can be used to screen DNA molecules, RNA molecules, peptide nucleic acids, peptides, mimetics, ribozymes, or proteins including transcription factors, enhancers, repressors, and the like which regulate the activity of the polynucleotide in the biological system. The assay involves providing a plurality of molecules and compounds, combining a polynucleotide or a composition of the invention with the plurality of molecules and compounds under conditions to allow specific binding, and detecting specific binding to identify at least one molecule or compound which specifically binds at least one polynucleotides of the invention.

Similarly the proteins, or portions thereof, can be used to screen a plurality or library of molecules or compounds in any of a variety of screening assays to identify a ligand. The protein employed in such screening can be free in solution, affixed to an abiotic substrate or expressed on the external, or a particular internal surface, of a bacterial, or other, cell. Specific binding between the protein and the ligand can be measured. The assay can be used to screen aptamers, DNA molecules, RNA molecules, peptide nucleic acids, peptides, mimetics, ribozymes, proteins, antibodies, agonists, antagonists, immunoglobulins, inhibitors, pharmaceutical agents or drug compounds and the like, which specifically bind the protein. One method for high throughput screening using very small assay volumes and very small amounts of test compound is described in Burbaum et al. U.S. Pat. No. 5,876,946, incorporated herein by reference, which screens large numbers of molecules for enzyme inhibition or receptor binding.

In one preferred embodiment, the polynucleotides are used for diagnostic purposes to determine the differential expression of a gene in a sample. The polynucleotide consists of complementary RNA and DNA molecules, branched nucleic acids, and/or PNAs. In one alternative, the polynucleotides are used to detect and quantify gene expression in biopsied samples in which differential expression of the polynucleotide indicates the presence of a disorder. In another alternative, the polynucleotide can be used to detect genetic polymorphisms associated with a disease. In a preferred embodiment, these polymorphisms are detected in an mRNA transcribed from an endogenous gene.

In another preferred embodiment, the polynucleotide is used as a probe. Specificity of the probe is determined by whether it is made from a unique region, a regulatory region, or from a region encoding a conserved motif. Both probe specificity and the stringency of the diagnostic hybridization or amplification will determine whether the probe identifies only naturally occurring, exactly complementary sequences, allelic variants, or related sequences. Probes designed to detect related sequences should preferably have at least 50% sequence identity to at least a fragment of a polynucleotide of the invention.

Methods for producing hybridization probes include the cloning of nucleic acid sequences into vectors for the production of RNA probes. Such vectors are known in the art, are commercially available, and can be used to synthesize RNA probes in vitro by adding RNA polymerases and labeled nucleotides. Probes can incorporate nucleotides labeled by a variety of reporter groups including, but not limited to, radionuclides such as $^{32}P$ or $^{35}S$, enzymatic labels such as alkaline phosphatase coupled to the probe via avidin/biotin coupling systems, fluorescent labels such as Cy3 and Cy5, and the like. The labeled polynucleotides can be used in Southern or northern analysis, dot blot, or other membrane-based technologies, on chips or other substrates, and in PCR technologies. Hybridization probes are also useful in mapping the naturally occurring genomic sequence. Fluorescent in situ hybridization (FISH) can be correlated with other physical chromosome mapping techniques and genetic map data as described in Heinz-Ulrich et al. (In: Meyers, supra, pp. 965–968). In many cases, genomic context helps identify genes that are encode a particular protein family. (See, e.g., Kirschning et al. (1997) Genomics 46:416–25.)

The polynucleotide can be labeled using standard methods and added to a sample from a subject under conditions for the formation and detection of hybridization complexes. After incubation the sample is washed, and the signal associated with complex formation is quantitated and compared with at least one standard value. Standard values are derived from any control sample, typically one that is free of the suspect disorder and from diseased samples, preferably from samples each of which represents a single, specific and preferably, staged disorder. If the amount of signal in the subject sample is altered in comparison to the standard values, then differential expression in the biopsied sample indicates the presence of the disorder. Qualitative and quantitative methods for comparing complex formation in subject samples with previously established standards are well known in the art.

Such assays can also be used to evaluate the efficacy of a particular therapeutic treatment regimen in animal studies, in clinical trials, or to monitor the treatment of an individual subject. Once the presence of disease is established and a treatment protocol is initiated, hybridization or amplification assays can be repeated on a regular basis to determine gene expression in the patient begins to approximate that which is observed in a healthy subject. The results obtained from successive assays can be used to show the efficacy of treatment over a period ranging from several hours, e.g. in the case of toxic shock, to many years ,e.g. in the case of osteoarthritis.

The polynucleotides can be used on a substrate such as a microarray to monitor gene expression, to identify splice variants, mutations, and polymorphisms. Information derived from analyses of expression patterns can be used to determine gene function, to understand the genetic basis of a disease, to diagnose a disorder, and to develop and monitor the activities of therapeutic agents used to treat a disorder. Microarrays can also be used to detect genetic diversity, single nucleotide polymorphisms, which may characterize a particular population, at the genomic level.

In another embodiment, antibodies or Fabs comprising an antigen binding site that specifically binds the protein can be used for the diagnosis of diseases characterized by the differential expression of the protein. A variety of protocols for measuring protein expression, including ELISAs, RIAs, and FACS, are well known in the art and provide a basis for diagnosing altered or abnormal levels of expression. Standard values for protein expression parallel those reviewed above for nucleotide expression. The amount of complex formation can be quantitated by various methods, preferably by photometric means. Quantities of the protein expressed in subject samples are compared with standard values. Deviation between standard and subject values establishes the parameters for diagnosing or monitoring a particular disorder. Alternatively, one can use competitive drug screening assays in which neutralizing antibodies capable of binding specifically with the protein compete with a test compound. Antibodies can be used to detect the presence of any peptide which shares one or more epitopes or antigenic determinants with the protein. In one aspect, the antibodies of the present invention can be used for treatment , delivery of therapeutics, or monitoring therapy for inflammatory disorders.

In another aspect, the polynucleotide, or its complement, can be used therapeutically for the purpose of expressing mRNA and protein, or conversely to block transcription or translation of the mRNA. Expression vectors can be constructed using elements from retroviruses, adenoviruses, herpes or vaccinia viruses, or bacterial plasmids, and the like. These vectors can be used for delivery of nucleotide sequences to a particular target cell population, tissue, or organ. Methods well known to those skilled in the art can be used to construct vectors to express the polynucleotides or their complements. (See, e.g., Maulik et al. (1997) *Molecular Biotechnology, Therapeutic Applications and Strategies*, Wiley-Liss, New York N.Y.) Alternatively, the polynucleotide or its complement, can be used for somatic cell or stem cell gene therapy. Vectors can be introduced in vivo, in vitro, and ex vivo. For ex vivo therapy, vectors are introduced into stem cells taken from the subject, and the resulting transgenic cells are clonally propagated for autologous transplant back into that same subject. Delivery of the polynucleotide by transfection, liposome injections, or polycationic amino polymers can be achieved using methods which are well known in the art. (See, e.g., Goldman et al. (1997) Nature Biotechnology 15:462–466.) Additionally, endogenous gene expression can be inactivated using homologous recombination methods which insert an inactive gene sequence into the coding region or other targeted region of the genome (See, e.g. Thomas et al. (1987) Cell 51: 503–512.) Vectors containing the polynucleotide can be transformed into a cell or tissue to express a missing protein or to replace a nonfunctional protein. Similarly a vector constructed to express the complement of the polynucleotide can be transformed into a cell to downregulate protein expression. Complementary or antisense sequences can consist of an oligonucleotide derived from the transcription initiation site; nucleotides between about positions −10 and +10 from the ATG are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee et al. In: Huber and Carr (1994) *Molecular and Immunologic Approaches*, Futura Publishing, Mt. Kisco N.Y., pp. 163–177.)

Ribozymes, enzymatic RNA molecules, can also be used to catalyze the cleavage of mRNA and decrease the levels of particular mRNAs, such as those comprising the polynucleotides of the invention. (See, e.g., Rossi (1994) Current Biology 4: 469–471.) Ribozymes can cleave mRNA at specific cleavage sites. Alternatively, ribozymes can cleave mRNAs at locations dictated by flanking regions that form complementary base pairs with the target mRNA. The construction and production of ribozymes is well known in the art and is described in Meyers (supra).

RNA molecules can be modified to increase intracellular stability and half-life. Possible modifications include, but are not limited to, the addition of flanking sequences at the 5' and/or 3' ends of the molecule, or the use of phosphorothioate or 2' O-methyl rather than phosphodiester linkages within the backbone of the molecule. Alternatively, nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases, can be included.

Further, an antagonist, or an antibody that binds specifically to the protein can be administered to a subject to treat an inflammatory disorder. The antagonist, antibody, or fragment can be used directly to inhibit the activity of the protein or indirectly to deliver a therapeutic agent to cells or tissues which express the protein. The therapeutic agent can be a cytotoxic agent selected from a group including, but not limited to, abrin, ricin, doxorubicin, daunorubicin, taxol, ethidium bromide, mitomycin, etoposide, tenoposide, vincristine, vinblastine, colchicine, dihydroxy anthracin dione, actinomycin D, diphteria toxin, Pseudomonas exotoxin A and 40, radioisotopes, and glucocorticoid.

Antibodies to the protein can be generated using methods that are well known in the art. Such antibodies can include, but are not limited to, polyclonal, monoclonal, chimeric, and single chain antibodies, Fab fragments, and fragments produced by a Fab expression library. Neutralizing antibodies, such as those which inhibit dimer formation, are especially preferred for therapeutic use. Monoclonal antibodies to the protein can be prepared using any technique which provides for the production of antibody molecules by continuous cell lines in culture. These include, but are not limited to, the hybridoma, the human B-cell hybridoma, and the EBV-hybridoma techniques. In addition, techniques developed for the production of chimeric antibodies can be used. (See, e.g., Pound (1998) *Immunochemical Protocols*, Methods Mol Biol Vol. 80). Alternatively, techniques described for the production of single chain antibodies can be employed. Fabs which contain specific binding sites for the protein can also be generated. Various immunoassays can be used to identify antibodies having the desired specificity. Numerous protocols for competitive binding or immunoradiometric assays using either polyclonal or monoclonal antibodies with established specificities are well known in the art.

Yet further, an agonist of the protein can be administered to a subject to treat or prevent a disease associated with decreased expression, longevity or activity of the protein.

An additional aspect of the invention relates to the administration of a pharmaceutical or sterile composition, in conjunction with a pharmaceutically acceptable carrier, for any of the therapeutic applications discussed above. Such pharmaceutical compositions can consist of the protein or antibodies, mimetics, agonists, antagonists, or inhibitors of the protein. The compositions can be administered alone or in combination with at least one other agent, such as a stabilizing compound, which can be administered in any sterile, biocompatible pharmaceutical carrier including, but not limited to, saline, buffered saline, dextrose, and water. The compositions can be administered to a subject alone or in combination with other agents, drugs, or hormones.

The pharmaceutical compositions utilized in this invention can be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions can contain pharmaceutically-acceptable carriers comprising excipients and auxiliaries which facilitate processing of the active compounds into preparations which can be used pharmaceutically. Further details on techniques for formulation and administration can be found in the latest edition of *Remington's Pharmaceutical Sciences* (Mack Publishing, Easton Pa.).

For any compound, the therapeutically effective dose can be estimated initially either in cell culture assays or in animal models such as mice, rats, rabbits, dogs, or pigs. An animal model can also be used to determine the concentration range and route of administration. Such information can then be used to determine useful doses and routes for administration in humans.

A therapeutically effective dose refers to that amount of active ingredient which ameliorates the symptoms or condition. Therapeutic efficacy and toxicity can be determined by standard pharmaceutical procedures in cell cultures or with experimental animals, such as by calculating and contrasting the $ED_{50}$ (the dose therapeutically effective in 50% of the population) and $LD_{50}$ (the dose lethal to 50% of the population) statistics. Any of the therapeutic compositions described above can be applied to any subject in need of such therapy, including, but not limited to, mammals such as dogs, cats, cows, horses, rabbits, monkeys, and most preferably, humans.

Stem Cells and Their Use

SEQ ID NOs:1–11 can be useful in the differentiation of stem cells. Eukaryotic stem cells are able to differentiate into the multiple cell types of various tissues and organs and to play roles in embryogenesis and adult tissue regeneration (Gearhart (1998) Science 282:1061–1062; Watt and Hogan (2000) Science 287:1427–1430). Depending on their source and developmental stage, stem cells can be totipotent with the potential to create every cell type in an organism and to generate a new organism, pluripotent with the potential to give rise to most cell types and tissues, but not a whole organism; or multipotent cells with the potential to differentiate into a limited number of cell types. Stem cells can be transfected with polynucleotides which can be transiently expressed or can be integrated within the cell as transgenes.

Embryonic stem (ES) cell lines are derived from the inner cell masses of human blastocysts and are pluripotent (Thomson et al. (1998) Science 282:1145–1147). They have normal karyotypes and express high levels of telomerase which prevents senescence and allows the cells to replicate indefinitely. ES cells produce derivatives that give rise to embryonic epidermal, mesodermal and endodermal cells. Embryonic germ (EG) cell lines, which are produced from primordial germ cells isolated from gonadal ridges and mesenteries, also show stem cell behavior (Shamblott et al. (1998) Proc Natl Acad Sci 95:13726–13731). EG cells have normal karyotypes and appear to be pluripotent.

Organ-specific adult stem cells differentiate into the cell types of the tissues from which they were isolated. They maintain their original tissues by replacing cells destroyed from disease or injury. Adult stem cells are multipotent and under proper stimulation can be used to generate cell types of various other tissues (Vogel (2000) Science 287:1418–1419). Hematopoietic stem cells from bone marrow provide not only blood and immune cells, but can also be induced to transdifferentiate to form brain, liver, heart, skeletal muscle and smooth muscle cells. Similarly mesenchymal stem cells can be used to produce bone marrow, cartilage, muscle cells, and some neuron-like cells, and stem cells from muscle have the ability to differentiate into muscle and blood cells (Jackson et al. (1999) Proc Natl Acad Sci 96:14482–14486). Neural stem cells, which produce neurons and glia, can also be induced to differentiate into heart, muscle, liver, intestine, and blood cells (Kuhn and Svendsen (1999) BioEssays 21:625–630); Clarke et al. (2000) Science 288:1660–1663; Gage (2000) Science 287:1433–1438; and Galli et al. (2000) Nature Neurosci 3:986–991).

Neural stem cells can be used to treat neurological disorders such as Alzheimer disease, Parkinson disease, and multiple sclerosis and to repair tissue damaged by strokes and spinal cord injuries. Hematopoietic stem cells can be used to restore immune function in immunodeficient patients or to treat autoimmune disorders by replacing autoreactive immune cells with normal cells to treat diseases such as multiple sclerosis, scleroderma, rheumatoid arthritis, and systemic lupus erythematosus. Mesenchymal stem cells can be used to repair tendons or to regenerate cartilage to treat arthritis. Liver stem cells can be used to repair liver damage. Pancreatic stem cells can be used to replace islet cells to treat diabetes. Muscle stem cells can be used to regenerate muscle to treat muscular dystrophies (Fontes and Thomson (1999) BMJ 319:1–3; Weissman (2000) Science 287:1442–1446 Marshall (2000) Science 287:1419–1421; Marmont (2000) Ann Rev Med 51:115–134).

EXAMPLES

It is to be understood that this invention is not limited to the particular devices, machines, materials and methods described. Although particular embodiments are.described, equivalent embodiments can be used to practice the invention. The described embodiments are provided to illustrate the invention and are not intended to limit the scope of the invention which is limited only by the appended claims.

I cDNA Library Construction

The cDNA library, OVARTUT05, was selected as an example to demonstrate the construction of the cDNA libraries from which the sequences used to identify genes associated with inflammatory disorders were derived. The OVARTUT05 library was constructed from tumorous ovary tissue obtained from a 62 year-old Caucasian female. Pathology indicated a grade 4 endometrioid carcinoma with extensive squamous differentiation forming a solid mass in the right ovary. The cervix showed mild chronic cervicitis, and the posterior uterine serosa showed focal endometriosis. Prior pathology indicated weakly proliferative endometrium with excessive stromal breakdown in the uterus and a mild chronic cervicitis with prominent nabothian cyst in the cervix.

The frozen tissue was homogenized and lysed using a POLYTRON homogenizer (Brinkmann Instruments, Westbury N.Y.) in guanidinium isothiocyanate solution. The lysate was centrifuged over a 5.7 M CsCl cushion using an SW28 rotor in a L8-70M ultracentrifuge (Beckman Coulter, Fullerton Calif.) for 18 hours at 25,000 rpm at ambient temperature. The RNA was extracted with acid phenol, pH 4.7, precipitated using 0.3 M sodium acetate and 2.5 volumes of ethanol, resuspended in RNAse-free water, and DNAse treated at 37C. The RNA extraction was repeated. The mRNA was isolated with the OLIGOTEX kit (Qiagen, Chatsworth Calif.) and used to construct the cDNA library.

The mRNA was handled according to the recommended protocols in the SUPERSCRIPT plasmid system (Life Technologies). The cDNAs were fractionated on a SEPHAROSE CL4B column (Amersham Pharmacia Biotech (APB), Piscataway N.J.), and those cDNAs exceeding 400 bp were ligated into pINCY plasmid (Incyte Genomics, Palo Alto Calif.). The plasmid was then transformed into DH5α competent cells (Life Technologies).

II Isolation and Sequencing of cDNA Clones

Plasmid DNA was released from the bacterial cells and purified using the REAL PREP 96 plasmid kit (Qiagen). This kit enabled the simultaneous purification of 96 samples in a 96-well block using multi-channel reagent dispensers. The recommended protocol was employed except for the following changes: 1) the bacteria were cultured in I ml of sterile TERRIFIC BROTH (BD Biosciences, San Jose Calif.) with carbenicillin at 25 mg/L and glycerol at 0.4%; 2) after inoculation and incubation for 19 hours, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4C.

The cDNAs were prepared using a MICROLAB 2200 system (Hamilton, Reno Nev.) in combination with DNA ENGINE thermal cyclers (MJ Research, Watertown Mass.). The cDNAs were sequenced by the method of Sanger and Coulson (1975; J Mol Biol 94:441–448) using ABI PRISM 377 DNA sequencing systems (Applied Biosystems). Most of the sequences were sequenced using standard ABI protocols and kits at solution volumes of 0.25×1.0×. In the alternative, some of the sequences were sequenced using solutions and dyes from APB.

III Selection, Assembly, and Characterization of Sequences

The sequences used for co-expression analysis were assembled from EST sequences, 5' and 3' long read sequences, and full length coding sequences. Of the 41,419 assembled sequences used in the analysis, each was expressed in at least five cDNA libraries.

The assembly process is described as follows. EST sequence chromatograms were processed and verified. Quality scores were obtained using PHRED (Ewing et al. (1998) Genome Res 8:175–185; Ewing and Green (1998) Genome Res 8:186–194), and edited sequences were loaded into a relational database management system (RDBMS). The sequences were clustered using BLAST with a product score of 50. All clusters of two or more sequences created a bin which represents one transcribed gene.

Assembly of the component sequences within each bin was performed using a modification of Phrap, a publicly available program for assembling DNA fragments (Green, P. University of Washington, Seattle Wash.). Bins that showed 82% identity from a local pair-wise alignment between any of the consensus sequences were merged.

Bins were annotated by screening the consensus sequence in each bin against public databases, such as GBpri and GenPept from NCBI. The annotation process involved a FASTn screen against the GBpri database in GenBank. Those hits with a percent identity of greater than or equal to 75% and an alignment length of greater than or equal to 100 base pairs were recorded as homolog hits. The residual unannotated sequences were screened by FASTx against GenPept. Those hits with an E value of less than or equal to $10^8$ were recorded as homolog hits.

Sequences were then reclustered using BLASTn and Cross-Match, a program for rapid amino acid and nucleic acid sequence comparison and database search (Green, supra), sequentially. Any BLAST alignment between a sequence and a consensus sequence with a score greater than 150 was realigned using cross-match. The sequence was added to the bin whose consensus sequence gave the highest Smith-Waterman score (Smith et al. (1992) Protein Engineering 5:35–51) amongst local alignments with at least 82% identity. Non-matching sequences were moved into new bins, and assembly processes were repeated.

IV Homology Searching of Polynucleotides and Their Encoded Proteins.

The polynucleotides of the Sequence Listing or their encoded proteins were used to query databases such as GenBank, SwissProt, BLOCKS, and the like. These databases that contain previously identified and annotated sequences or domains were searched using BLAST or BLAST 2 (Altschul et al. supra; Altschul, supra) to produce alignments and to determine which sequences were exact matches or homologs. The alignments were to sequences of prokaryotic (bacterial) or eukaryotic (animal, fungal, or plant) origin. Alternatively, algorithms such as the one described in Smith and Smith (1992, Protein Engineering 5:35–51) could have been used to deal with primary sequence patterns and secondary structure gap penalties. All of the sequences disclosed in this application have lengths of at least 49 nucleotides, and no more than 12% uncalled bases (where N is recorded rather than A, C, G, or T).

As detailed in Karlin (supra), BLAST matches between a query sequence and a database sequence were evaluated statistically and only reported when they satisfied the threshold of $10^{-25}$ for nucleotides and $10^{-4}$ for peptides. Homology was also evaluated by product score calculated as follows: the % nucleotide or amino acid identity [between the query and reference sequences] in BLAST is multiplied by the % maximum possible BLAST score [based on the lengths of query and reference sequences] and then divided by 100. In comparison with hybridization procedures used in the laboratory, the electronic stringency for an exact match was set at 70, and the conservative lower limit for an exact match was set at approximately 40 (with 1–2% error due to uncalled bases).

The BLAST software suite, freely available sequence comparison algorithms (NCBI, Bethesda Md.; http://www.ncbi.nlm.nih.gov/gorf/b12.html), includes various sequence analysis programs including "blastn" that is used to align nucleic acid molecules and BLAST 2 that is used for direct pairwise comparison of either nucleic or amino acid molecules. BLAST programs are commonly used with gap and other parameters set to default settings, e.g.: Matrix: BLOSUM62; Reward for match: 1; Penalty for mismatch: -2; Open Gap: 5 and Extension Gap: 2 penalties; Gap x drop-off: 50; Expect: 10; Word Size: 11; and Filter: on. Identity or similarity is measured over the entire length of a sequence or some smaller portion thereof. Brenner et al. (1998; Proc Natl Acad Sci 95:6073–6078, incorporated herein by reference) analyzed the BLAST for its ability to identify structural homologs by sequence identity and found 30% identity is a reliable threshold for sequence alignments of at least 150 residues and 40%, for alignments of at least 70 residues.

The polynucleotides of this application were compared with assembled consensus sequences or templates found in the LIFESEQ GOLD database. Component sequences from cDNA, extension, full length, and shotgun sequencing projects were subjected to PHRED analysis and assigned a quality score. All sequences with an acceptable quality score were subjected to various pre-processing and editing pathways to remove low quality 3' ends, vector and linker sequences, polyA tails, Alu repeats, mitochondrial and ribosomal sequences, and bacterial contamination sequences. Edited sequences had to be at least 50 bp in length, and low-information sequences and repetitive elements such as dinucleotide repeats, Alu repeats, and the like, were replaced by "Ns" or masked.

Edited sequences were subjected to assembly procedures in which the sequences were assigned to gene bins. Each sequence could only belong to one bin, and sequences in each bin were assembled to produce a template. Newly sequenced components were added to existing bins using BLAST and CROSSMATCH. To be added to a bin, the component sequences had to have a BLAST quality score greater than or equal to 150 and an alignment of at least 82% local identity. The sequences in each bin were assembled using PHRAP. Bins with several overlapping component sequences were assembled using DEEP PHRAP. The orientation of each template was determined based on the number and orientation of its component sequences.

Bins were compared to one another and those having local similarity of at least 82% were combined and reassembled. Bins having templates with less than 95% local identity were split. Templates were subjected to analysis by STITCHER/EXON MAPPER algorithms that analyze the probabilities of the presence of splice variants, alternatively spliced exons, splice junctions, differential expression of alternative spliced genes across tissue types or disease states, and the like. Assembly procedures were repeated periodically, and templates were annotated using BLAST against GenBank databases such as GBpri. An exact match was defined as having from 95% local identity over 200 base pairs through 100% local identity over 100 base pairs and a homolog match as having an E-value (or probability score) of $\leq 1 \times 10^{-8}$. The templates were also subjected to frameshift FASTx against GENPEPT, and homolog match was defined as having an E-value of $\leq 1 \times 10^{-8}$. Template analysis and assembly was described in U.S. Ser. No. 09/276,534, filed Mar. 25, 1999.

Following assembly, templates were subjected to BLAST, motif, and other functional analyses and categorized in protein hierarchies using methods described in U.S. Ser. No. 08/812,290 and U.S Ser. No. 08/811,758iled Mar. 6, 1997; in U.S. Ser. No. 08/947,845, filed Oct. 9, 1997; and in U.S. Ser. No. 09/034,807, filed Mar. 4, 1998. Then templates were analyzed by translating each template in all three forward reading frames and searching each translation against the PFAM database of hidden Markov model-based protein families and domains using the HMMER software package (Washington University School of Medicine, St. Louis Mo.; http://pfam.wustl.edu/).

The polynucleotide was further analyzed using MACDNASIS PRO software (Hitachi Software Engineering), and LASERGENE software (DNASTAR) and queried against public databases such as the GenBank rodent, mammalian, vertebrate, prokaryote, and eukaryote databases, SwissProt, BLOCKS, PRINTS, PFAM, and Prosite.

V Description of Genes Known to be Associated With Inflammatory Disorders

Eleven known inflammation genes were selected to identify novel genes that are closely associated with inflammation. These known genes, CD16, L-selectin, SLAP, IP-30, p67phox, p47phox, p40phox, AAT, Clq-A, FLAP, and HCK are described below.

| Gene | Description & References |
|------|--------------------------|
| CD16 | receptor for IgG a.k.a. FcgammaRIII; phagocytosis of complement-generated immune complexes occurs through CD16 (Tamm et al. (1996) J Biol Chem 271:3659–66; Marsh et al. (1998) J Immunol 160:3942–8) |
| L-selectin | Leukocyte adhesion molecule, binds carbohydrate ligand on endothelial cell glycoprotein Adhesion is required for extravasation near inflammation site; auxiliary function in neutrophil activation during inflammation (Frohlich et al. (1998) Blood 91:2558–64; Girard and Amalric (1998) Adv Exp Med Biol 435:55–62) |
| SLAP | Src-like adapter protein; associated with Eck RPTK transduction pathway; Eck RPTK autocrine loop implicated in inflammation (Pandey et al. (1995) J Biol Chem 270:19201–4; Pandey et al. (1995) Science 268:567–9) |
| IP-30 | Functions in MHC Class II processing of peptides, implicated in inflammation and α-interferon inducible (Luster et al. (1988) J Biol Chem 263:12036–43; Arunachalam et al. (1998) J Immunol 160:5797–806; Schuelke et al. (1998) Biochem Biophys Res Commun 245:599–606) |
| p67phox | superoxidase holoenzyme subunits; macrophages utilize reactive superoxide in |
| p47phox | degradation of phagocytosed matter; phox subunits induced by complement during |
| p40phox | inflammation (Ratnam and Mookerjea (1998) Immunology 94:560–568) |
| AAT | alpha-1-antitrypsin inhibits trypsin, a protease; differentially expressed in inflammation Several alleles linked to chronic inflammatory disorders; (Breit and Penny (1980) Aust N Z J Med 10:449–53; Takeuchi et al. (1984) Int J Tissue React 6:1–8) |
| Clq-A | First complement component, subcomponent q, subunit A (Alberts et al. (1994) Molecular Biology of the Cell, Garland Publishing, New York NY, p. 1214) |
| FLAP | 5-lipoxygenase activating protein; lipoxygenase enzyme catalyzes formation of leukotrienes which are potent inflammatory mediators. FLAP is an anti-inflammatory therapeutic target (Byrum et al. (1997) J Exp Med 185:1065–75; Muller-Peddinghaus (1997) J Physiol Pharmacol 48:529–36) |

-continued

| Gene | Description & References |
|------|--------------------------|
| HCK | Src-family tyrosine kinase specific to hematopoietic cells; functions in integrin signaling Mouse knockouts have impaired inflammation response (Lowell and Berton (1998) Proc Natl Acad Sci 95:7580–84) |

VI Co-expression Among Known Marker Genes and Novel Polynucleotides

The co-expression of the 11 known genes with each other is shown below. The entries are the negative log of the p-value (−log p) for the co-expression of the two genes. As shown, co-expression analysis successfully identified the strong association among the known genes which indicates that co-expression analysis was effective in identifying genes that are highly associated with inflammation and inflammatory disorders. The degree of association was measured by probability values and the cutoff p-value used in this analysis was less than 0.00001.

Using the LIFESEQ GOLD database (Incyte Genomics), the method also identified polynucleotides from among a total of 41,419 assembled sequences that show strong association with the known genes. The process was reiterated until the number of polynucleotides was reduced to the final eleven polynucleotides shown below. The following tabular entries show the negative log of the p-value (−log p) for the co-expression among the known marker genes and the novel polynucleotides. The novel polynucleotides are identified in the table below by their Incyte clone numbers and the known genes their abbreviated names as shown in Example IV above. For each polynucleotide, the p-value is the probability that the observed co-expression is due to chance, using the Fisher Exact Test.

| Gene or SEQ ID NO (clone) | CD16 | L-selectin | SLAP | IP-30 | p67-phox | AA | p47-phox | C1q | p40-phox | FLA | HC | 1221361 | 3055142 | 402234 |
|---|---|---|---|---|---|---|---|---|---|---|---|---|---|---|
| CD16 | | | | | | | | | | | | | | |
| L-selectin | 4 | | | | | | | | | | | | | |
| SLAP | 5 | 6 | | | | | | | | | | | | |
| IP-30 | 5 | 3 | 4 | | | | | | | | | | | |
| P67-phox | 3 | 5 | 7 | 13 | | | | | | | | | | |
| AAT | 6 | 2 | 4 | 10 | 5 | | | | | | | | | |
| P47-phox | 5 | 6 | 5 | 14 | 7 | 3 | | | | | | | | |
| C1qA | 7 | 2 | 6 | 11 | 3 | 7 | 6 | | | | | | | |
| P40-phox | 5 | 5 | 3 | 4 | 7 | 4 | 6 | 1 | | | | | | |
| FLAP | 7 | 5 | 3 | 11 | 5 | 3 | 5 | 7 | 3 | | | | | |
| HCK | 9 | 8 | 4 | 5 | 8 | 5 | 7 | 3 | 6 | 3 | | | | |
| 4 (1221361) | 3 | 5 | 7 | 4 | 3 | 1 | 4 | 2 | 4 | 2 | 4 | | | |
| 10 (3055142) | 6 | 5 | 9 | 4 | 5 | 3 | 8 | 1 | 4 | 3 | 8 | 4 | | |
| 1 (402234) | 3 | 6 | 4 | 4 | 2 | 0 | 6 | 1 | 3 | 4 | 2 | 3 | 1 | |
| 11 (3507924) | 2 | 5 | 3 | 4 | 4 | 8 | 4 | 1 | 7 | 3 | 2 | 3 | 2 | 4 |
| 5 (1335016) | 7 | 3 | 3 | 8 | 2 | 2 | 5 | 6 | 3 | 4 | 3 | 4 | 5 | 2 |
| 9 (3054032) | 5 | 11 | 9 | 5 | 4 | 4 | 7 | 7 | 7 | 8 | 7 | 5 | 7 | 5 |
| 2 (569989) | 4 | 4 | 4 | 6 | 9 | 1 | 8 | 2 | 4 | 5 | 4 | 4 | 4 | 7 |
| 6 (2349263) | 8 | 1 | 2 | 6 | 4 | 4 | 3 | 8 | 5 | 5 | 6 | 3 | 3 | 1 |
| 7 (2471716) | 3 | 5 | 3 | 7 | 5 | 1 | 7 | 4 | 5 | 2 | 4 | 3 | 5 | 4 |
| 8 (2726173) | 3 | 8 | 5 | 4 | 6 | 2 | 7 | 0 | 2 | 3 | 5 | 4 | 3 | 4 |
| 3 (706377) | 4 | 5 | 5 | 8 | 6 | 5 | 10 | 3 | 6 | 3 | 3 | 4 | 4 | 9 |

| Gene or SEQ ID NO (clone) | 3507924 | 1335016 | 3054032 | 569989 | 2349263 | 2471716 | 2726173 | 706377 |
|---|---|---|---|---|---|---|---|---|
| CD16 | | | | | | | | |
| L-selectin | | | | | | | | |
| SLAP | | | | | | | | |
| IP-30 | | | | | | | | |
| P67-phox | | | | | | | | |
| AAT | | | | | | | | |
| P47-phox | | | | | | | | |
| C1qA | | | | | | | | |
| P40-phox | | | | | | | | |
| FLAP | | | | | | | | |
| HCK | | | | | | | | |
| 4 (1221361) | | | | | | | | |
| 10 (3055142) | | | | | | | | |
| 1 (402234) | | | | | | | | |
| 11 (3507924) | | | | | | | | |
| 5 (1335016) | 2 | | | | | | | |
| 9 (3054032) | 4 | 4 | | | | | | |
| 2 (569989) | 2 | 2 | 5 | | | | | |
| 6 (2349263) | 3 | 9 | 5 | 4 | | | | |
| 7 (2471716) | 5 | 4 | 8 | 3 | 7 | | | |
| 8 (2726173) | 4 | 2 | 3 | 3 | 2 | 5 | | |
| 3 (706377) | 4 | 5 | 5 | 7 | 3 | 6 | 3 | |

The highest co-expression value is obtained when the highest (−log p) value found along the horizontal line following each SEQ ID NO (clone number) are correlated with a known marker gene (abbreviation along the top line of the chart). For example Another look at the data above simplified by reducing it to a single highest co-expression (−log p) and naming at least one inflammatory disorder for each polynucleotide is shown below:

| Gene | SEQ ID NO | p-value* | Inflammatory Disorder |
| --- | --- | --- | --- |
| CD16 | 6 | 8 | rheumatoid arthritis |
| L-selectin | 1 | 6 | BPH |
| L-selectin | 8 | 8 | asthma |
| L-selectin | 9 | 11 | cholecystitis |
| SLAP | 4 | 7 | chronic heart failure (CHF) |
| SLAP | 10 | 9 | bacterial infection, toxic shock |
| IP-30 | 5 | 8 | chronic inflammation of bowel |
| IP-30 | 7 | 7 | immune response |
| P67-phox | 2 | 9 | hypereosinophilia |
| AAT | 11 | 8 | asthma |
| P47-phox | 3 | 10 | lung cancer and complications |

*(−log p) = 5 is very highly significant

VII Novel Polynucleotides Associated With Inflammatory Disorders

Eleven polynucleotides were found to be associated with known genes that are diagnostic markers for inflammation and inflammatory disorders. The polynucleotides comprising the nucleic acid sequences of SEQ ID NOs:1–11 were first identified as Incyte Clones 402234, 569989, 706377, 1221361, 1335016, 2349263, 2471716, 2726173, 3054032, 3055142, and 3507924, respectively. These sequences were assembled according to the procedures described in Example IV. BLAST and motif searches were performed for SEQ ID NOs:1–11 and SEQ ID NOs:12–17 according to Example V. Proteins or peptides comprising the amino acid sequences of SEQ ID NOs:12–17 were encoded by the nucleic acids of SEQ ID NO: 1, 2, 6, 7, 8, and 11, respectively.

SEQ ID NO:3 is 1229 nucleotides in length and shares about 99% sequence identity from about nucleotide 250 to about nucleotide 1216 with a human basement membrane-induced gene identified in a human endometrial adenocarcinoma cell line (g3132521).

SEQ ID NO:4 is about 1261 nucleotides in length and has about 34% sequence identity from nucleotide 23 to nucleotide 994 with a sequence similar to a RNA recognition motif (g2645068).

SEQ ID NO:5 is 1340 nucleotides in length and has about 60% sequence identity from about nucleotide 21 to about nucleotide 925 with a human prostaglandin transporter hPGT mRNA (g3006201). The protein encoded by SEQ ID NO:5 exhibits several potential transmembrane domains identified by HMM analysis.

SEQ ID NO:9 is 2309 nucleotides in length and shows sequence identity from about nucleotide 104 to about nucleotide 785 with a human polycystic kidney disease-associated protein gene (g790818).

SEQ ID NO:12 is 127 amino acid residues in length and shows about 50% sequence identity from about residue 37 to about residue 106 with a tobacco LIM-domain-containing protein.(g1841464). The LIM domain is a cysteine-rich, zinc-binding motif of about 60 amino-acid residues that plays a potential role in DNA binding and regulation (Perez-Alvarado et al. (1994) Nat Struct Biol 1:388–398). PFAM analysis shows that residues 40 to 97 of SEQ ID NO: 12 align with and encompass the LIM domain.

SEQ ID NO:13 is 93 amino acid residues in length and has a potential signal peptide from residue 1 to residue 18. SEQ ID NO:13 also exhibits a potential transmembrane domain from about residues 47 to residue 69.

SEQ ID NO:14 is 225 amino acid residues in length and has about 32% sequence identity from about residue 5 to about residue 135 with a mouse high affinity IgE receptor beta subunit (g309225).

SEQ ID NO:15 is 547 amino acid residues in length and has about 35% sequence identity from about residue 413 to about residue 546 with a rat beta-chimaerin, a GTPase-activating protein expressed exclusively in the testis at the onset of sexual maturation (g203117). PFAM analysis shows that SEQ ID NO:15 has sequence homology from about residue 353 to about residue 523 with the GTPase-activator protein for Rho-like GTPases.

SEQ ID NO:16 is 265 amino acid residues in length and shows about 93% sequence identity from about residue 39 to about residues 265 with Maxp1, a rat protein which interacts with Mss4, a guanine nucleotide exchange factor (g2459833), and about 91% sequence identity from about residue 38 to about residue 265 with. Norel, a mouse putative Ras effector that plays a role in transmitting growth and differentiation signals received from Ras proteins (g2997698). PFAM analysis confirms that SEQ ID NO:16 from about residue 1 19 to about residue 211 matches a Ras association domain which interacts directly with the Ras proteins.

SEQ ID NO:17 is 394 amino acid residues in length and exhibits a potential signal peptide sequence from about residue 1 to residue 19 and a potential transmembrane domain from about residues 273 to residue 295.

VIII Hybridization Technologies and Analyses

Immobilization of Polynucleotides on a Substrate The polynucleotides are applied to a substrate by one of the following methods. A mixture of polynucleotides is fractionated by gel electrophoresis and transferred to a nylon membrane by capillary transfer. Alternatively, the polynucleotides are individually ligated to a vector and inserted into bacterial host cells to form a library. The polynucleotides are then arranged on a substrate by one of the following methods. In the first method, bacterial cells containing individual clones are robotically picked and arranged on a nylon membrane. The membrane is placed on LB agar containing selective agent (carbenicillin, kanamycin, ampicillin, or chloramphenicol depending on the vector used) and incubated at 37C for 16 hr. The membrane is removed from the agar and consecutively placed colony side up in 10% SDS, denaturing solution (1.5 M NaCI, 0.5 M NaOH), neutralizing solution (1.5 M NaCl, 1 M Tris-HCl, pH 8.0), and twice in 2×SSC for 10 min each. The membrane is then UV irradiated in a STRATALINKER UV-crosslinker (Stratagene).

In the second method, polynucleotides are amplified from bacterial vectors by thirty cycles of PCR using primers complementary to vector sequences flanking the insert. PCR amplification increases a starting concentration of 1–2 ng nucleic acid to a final quantity greater than 5 μg. Amplified nucleic acids from about 400 bp to about 5000 bp in length are purified using SEPHACRYL400 beads (APB). Purified nucleic acids are arranged on a nylon membrane manually or using a dot/slot blotting manifold and suction device and are immobilized by denaturation, neutralization, and UV irradiation as described above. Purified nucleic acids are robotically arranged and immobilized on polymer-coated glass slides using the procedure described in U.S. Pat. No. 5,807, 522. Polymer-coated slides are prepared by cleaning glass microscope slides (Corning, Acton Mass.) by ultrasound in 0.1% SDS and acetone, etching in 4% hydrofluoric acid (VWR Scientific Products, West Chester Pa.), coating with 0.05% aminopropyl silane (Sigma-Aldrich) in 95% ethanol, and curing in a 110C oven. The slides are washed extensively with distilled water between and after treatments. The nucleic acids are arranged on the slide and then immobilized by exposing the array to UV irradiation using a STRATALINKER UV-crosslinker (Stratagene). Arrays are then washed at room temperature in 0.2% SDS and rinsed three times in distilled water. Non-specific binding sites are blocked by incubation of arrays in 0.2% casein in phosphate buffered saline (PBS; Tropix, Bedford Mass.) for 30 min at 60C; then the arrays are washed in 0.2% SDS and rinsed in distilled water as before.

Probe Preparation for Membrane Hybridization

Hybridization probes derived from the polynucleotides of the Sequence Listing are employed for screening cDNAs, mRNAs, or genomic DNA in membrane-based hybridizations. Probes are prepared by diluting the polynucleotides to a concentration of 40–50 ng in 45 µl TE buffer, denaturing by heating to 100C for five min, and briefly centrifuging. The denatured polynucleotide is then added to a REDIPRIME tube (APB), gently mixed until blue color is evenly distributed, and briefly centrifuged. Five µl of [$^{32}$P] dCTP is added to the tube, and the contents are incubated at 37C for 10 min. The labeling reaction is stopped by adding 5 µl of 0.2M EDTA, and probe is purified from unincorporated nucleotides using a PROBEQUANT G-50 microcolumn (APB). The purified probe is heated to 100C for five min, snap cooled for two min on ice, and used in membrane-based hybridizations as described below.

Probe Preparation for Polymer Coated Slide Hybridization

Hybridization probes derived from mRNA isolated from samples are employed for screening polynucleotides of the Sequence Listing in array-based hybridizations. Probe is prepared using the GEMbright kit (Incyte Genomics) by diluting mRNA to a concentration of 200 ng in 9 µl TE buffer and adding 5 µl 5×buffer, 1 µl 0.1 M DTT, 3 µl Cy3 or Cy5 labeling mix, 1 µl RNAse inhibitor, 1 µl reverse transcriptase, and 5 µl 1×yeast control mRNAs. Yeast control mRNAs are synthesized by in vitro transcription from noncoding yeast genomic DNA (W. Lei, unpublished). As quantitative controls, one set of control mRNAs at 0.002 ng, 0.02 ng, 0.2 ng, and 2 ng are diluted into reverse transcription reaction mixture at ratios of 1:100,000, 1:10,000, 1:1000, and 1:100 (w/w) to sample mRNA respectively. To examine mRNA differential expression patterns, a second set of control mRNAs are diluted into reverse transcription reaction mixture at ratios of 1:3, 3:1, 1:10, 10:1, 1:25, and 25:1 (w/w). The reaction mixture is mixed and incubated at 37C for two hr. The reaction mixture is then incubated for 20 min at 85C, and probes are purified using two successive CHROMA SPIN+TE 30 columns (Clontech, Palo Alto Calif.). Purified probe is ethanol precipitated by diluting probe to 90 µl in DEPC-treated water, adding 2 µl 1g/ml glycogen, 60 µl 5 M sodium acetate, and 300 µl 100% ethanol. The probe is centrifuged for 20 min at 20,800×g, and the pellet is resuspended in 12 µl resuspension buffer, heated to 65C for five min, and mixed thoroughly. The probe is heated and mixed as before and then stored on ice. Probe is used in high density array-based hybridizations as described below.

Membrane-based Hybridization

Membranes are pre-hybridized in hybridization solution containing 1% Sarkosyl and 1×high phosphate buffer (0.5 M NaCl, 0.1 M $Na_2HPO_4$, 5 mM EDTA, pH 7) at 55C for two hr. The probe, diluted in 15 ml fresh hybridization solution, is then added to the membrane. The membrane is hybridized with the probe at 55C for 16 hr. Following hybridization, the membrane is washed for 15 min at 25C in 1 mM Tris (pH 8.0), 1% Sarkosyl, and four times for 15 min each at 25C in 1 mM Tris (pH 8.0). To detect hybridization complexes, XOMAT-AR film (Eastman Kodak, Rochester N.Y.) is exposed to the membrane overnight at −70C, developed, and examined visually.

Polymer Coated Slide-based Hybridization

Probe is heated to 65C for five min, centrifuged five min at 9400 rpm in a 5415C microcentrifuge (Eppendorf Scientific, Westbury N.Y.), and then 18 µl are aliquoted onto the array surface and covered with a coverslip. The arrays are transferred to a waterproof chamber having a cavity just slightly larger than a microscope slide. The chamber is kept at 100% humidity internally by the addition of 140 µl of 5×SSC in a corner of the chamber. The chamber containing the arrays is incubated for about 6.5 hr at 60C. The arrays are washed for 10 min at 45C in 1×SSC, 0.1% SDS, and three times for 10 min each at 45C in 0.1×SSC, and dried.

Hybridization reactions are performed in absolute or differential hybridization formats. In the absolute hybridization format,.probe from one sample is hybridized to array elements, and signals are detected after hybridization complexes form. Signal strength correlates with probe mRNA levels in the sample. In the differential hybridization format, differential expression of a set of genes in two biological samples is analyzed. Probes from the two samples are prepared and labeled with different labeling moieties. A mixture of the two labeled probes is hybridized to the array elements, and signals are examined under conditions in which the emissions from the two different labels are individually detectable. Elements on the array that are hybridized to equal numbers of probes derived from both biological samples give a distinct combined fluorescence (Shalon WO95/35505).

Hybridization complexes are detected with a microscope equipped with an INNOVA 70 mixed gas 10 W laser (Coherent, Santa Clara Calif.) capable of generating spectral lines at 488 nm for excitation of Cy3 and at 632 nm for excitation of Cy5. The excitation laser light is focused on the array using a 20X microscope objective (Nikon, Melville N.Y.). The slide containing the array is placed on a computer-controlled X-Y stage on the microscope and raster-scanned past the objective with a resolution of 20 micrometers. In the differential hybridization format, the two fluorophores are sequentially excited by the laser. Emitted light is split, based on wavelength, into two photomultiplier tube detectors (PMT R1477, Hamamatsu Photonics Systems, Bridgewater N.J.) corresponding to the two fluorophores. Appropriate filters positioned between the array and the photomultiplier tubes are used to filter the signals. The emission maxima of the fluorophores used are 565 nm for Cy3 and 650 nm for Cy5. The sensitivity of the scans is calibrated using the signal intensity generated by the yeast control mRNAs added to the probe mix. A specific location on the array contains a complementary DNA sequence, allowing the intensity of the signal at that location to be correlated with a weight ratio of hybridizing species of 1:100,000.

The output of the photomultiplier tube is digitized using a 12-bit RTI-835H analog-to-digital (A/D) conversion board (Analog Devices, Norwood MA) installed in an IBM-compatible PC computer. The digitized data are displayed as an image where the signal intensity is mapped using a linear 20-color transformation to a pseudocolor scale ranging from blue (low signal) to red (high signal). The data is also analyzed quantitatively. Where two different fluorophores are excited and measured simultaneously, the data are first corrected for optical crosstalk (due to overlapping emission spectra) between the fluorophores using the emission spectrum for each fluorophore. A grid is superimposed over the fluorescence signal image such that the signal from each spot is centered in each element of the grid. The fluorescence signal within each element is then integrated to obtain a numerical value corresponding to the average intensity of the signal. The software used for signal analysis is the GEMTOOLS program (Incyte Genomics).

IX Transcript Imaging

The transcript images for SEQ ID NOs:1, 2, 3, and 6 were performed using the LIFESEQ GOLD database (Incyte Genomics). The product score for sequences was calculated as follows: the BLAST score is multiplied by the % nucleotide identity and the product is divided by (5 times the length of the shorter of the two sequences), such that a 100% alignment over the length of the shorter sequence gives a product score of 100. A product score of 70, which assures an exact match, was the cut-off score for the transcript images.

All sequences and cDNA libraries in the LIFESEQ database were categorized by system, organ/tissue and cell type. The categories included cardiovascular system, connective tissue, digestive system, embryonic structures, endocrine system, exocrine glands, female and male reproductive, germ cells, hemic/immune system, liver, musculoskeletal system, nervous system, pancreas, respiratory system, sense organs, skin, stomatognathic system, unclassified/mixed, and the urinary tract. For each category, the number of libraries in which the sequence was expressed were counted and shown over the total number of libraries in that category. All normalized or pooled libraries, which have high copy number sequences removed prior to processing. All mixed or pooled tissues, which are considered non-specific in that they contain more than one tissue type or more than one subject's tissue, were excluded from this analysis. Cell lines and fetal tissues were generally not considered.

For purposes of example, the four transcript images below show independent confirmation of the results of the co-expression analysis. The transcript images demonstrate differential expression of SEQ ID NOs:1, 2, 3 and 6, each in a different category, as produced using the LIFESEQ GOLD database (Incyte Genomics).

| SEQ ID NO:1 (Category: Male Reproductive) | | | | |
|---|---|---|---|---|
| Library | cDNAs | Description | Abundance | % Abundance |
| PROSDIP01 | 487 | prostate, stroma, BPH, M, 3' CGAP | 3 | 0.6160 |
| PROSTUP02 | 869 | prostate tumor, M, 3' CGAP | 1 | 0.1151 |
| PROSTUT01 | 3224 | prostate tumor, adenoCA, 50M | 1 | 0.0310 |
| PROSNOT26 | 3695 | prostate, mw/adenoCA, 65M | 1 | 0.0271 |

SEQ ID NO:1 is differentially expressed in benign prostate hyperplasia. Expression exceeds that of any other prostate library, including tumor and cytologically normal tissue, by greater than five-fold.

| SEQ ID NO:2 (Category: Hemic/Immune) | | | | |
|---|---|---|---|---|
| Library | cDNAs | Description | Abundance | % Abundance |
| EOSIHET02 | 9261 | periph blood, hypereosinophilia, 48M | 2 | 0.0216 |
| EOSITXT01 | 8976 | periph blood, eosinophils, t/IL-5 | 1 | 0.0111 |

SEQ ID NO:2 is differentially expressed in hypereosinophilia, even exceeding IL-5 activated expression by approximately two-fold.

| SEQ ID NO:3 (Category: Respiratory System) | | | | |
|---|---|---|---|---|
| Library | cDNAs | Description | Abundance | % Abundance |
| LUNGTUT13 | 3990 | lung tumor, adenoCA, 47M | 2 | 0.0501 |
| LUNGNOT38 | 3447 | lung, asthma, 15M | 1 | 0.0290 |
| LUNGNOT03 | 4959 | lung, mw/mets thyroid CA, 79M | 1 | 0.0202 |
| LUNLTMT01 | 6668 | lung, mw/adenoCA, aw/node mets, 63F | 1 | 0.0150 |

SEQ ID NO:3 is differentially expressed in adenocarcinoma of the lung. Expression exceeds that seen in asthmatic and cytologically normal lung by approximately two-fold.

| SEQ ID NO:6 (Category: Musculoskeletal System) | | | | |
|---|---|---|---|---|
| Library | cDNAs | Description | Abundance | % Abundance |
| SYNWDIT01 | 3232 | synovium, wrist, dorsal, rheuA, 64F | 4 | 0.1238 |
| SYNORAB01 | 5140 | synovium, hip, rheuA, 68F | 6 | 0.1167 |
| SYNORAT03 | 5814 | synovium, wrist, rheuA, 56F | 6 | 0.1032 |
| SYNORAT04 | 5665 | synovium, wrist, rheuA, 62F | 3 | 0.0530 |

SEQ ID NO:6 was differentially expressed in the synovium afflicted with rheumatoid arthritis. The sequence was not highly expressed in association with libraries with designated osteoarthritis or in cultured chrondrocytes.

X Complementary Molecules

The complement of the novel polynucleotide, from about 5 bp (e.g., a PNA) to about 5000 bp (e.g., the complement of a cDNA insert), are used to detect or inhibit gene expression. These molecules are selected using LASERGENE software (DNASTAR). Detection is described in Example VIII. To inhibit transcription by preventing promoter binding, the complementary molecule is designed to bind to the most unique 5' sequence and includes nucleotides of the 5' UTR upstream of the initiation codon of the open reading frame. Complementary molecules include genomic sequences (such as enhancers or introns) and are used in "triple helix" base pairing to compromise the ability of the double helix to open sufficiently for the binding of polymerases, transcription factors, or regulatory molecules. To inhibit translation, a complementary molecule is designed to prevent ribosomal binding to the mRNA encoding the protein.

Complementary molecules are placed in expression vectors and used to transform a cell line to test efficacy; into an organ, tumor, synovial cavity, or the vascular system for transient or short term therapy; or into a stem cell, zygote, or other reproducing lineage for long term or stable gene therapy. Transient expression lasts for a month or more with a non-replicating vector and for three months or more if appropriate elements for inducing vector replication are used in the transformation/expression system.

Stable transformation of appropriate dividing cells with a vector encoding the complementary molecule produces a transgenic cell line, tissue, or organism (U.S. Pat. No. 4,736,866). Those cells that assimilate and replicate sufficient quantities of the vector to allow stable integration also produce enough complementary molecules to compromise or entirely eliminate activity of the polynucleotide encoding the protein.

XI Protein Expression

Expression and purification of the protein are achieved using either a cell expression system or an insect cell expression system. The pUB6/V5-His vector system (Invitrogen, Carlsbad Calif.) is used to express protein in CHO cells. The vector contains the selectable bsd gene, multiple cloning sites, the promoter/enhancer sequence from the human ubiquitin C gene, a C-terminal V5 epitope for antibody detection with anti-V5 antibodies, and a C-terminal polyhistidine (6xHis) sequence for rapid purification on PROBOND resin (Invitrogen). Transformed cells are selected on media containing blasticidin.

*Spodoptera frugiperda* (Sf9) insect cells are infected with recombinant Autographica californica nuclear polyhedrosis virus (baculovirus). The polyhedrin gene is replaced with the polynucleotide by homologous recombination and the polyhedrin promoter drives transcription. The protein is synthesized as a fusion protein with 6xhis which enables purification as described above. Purified protein is used in the following activity and to make antibodies.

XII Production of Antibodies

The protein is purified using polyacrylamide gel electrophoresis and used to immunize mice or rabbits.

Antibodies are produced using the protocols below. Alternatively, the amino acid sequence of the expressed protein is analyzed using LASERGENE software (DNASTAR) to determine regions of high antigenicity. An antigenic epitope, usually found near the C-terminus or in a hydrophilic region is selected, synthesized, and used to raise antibodies. Typically, epitopes of about 15 residues in length are produced using an ABI 431A peptide synthesizer (Applied Biosystems) using Fmoc-chemistry and coupled to KLH (Sigma-Aldrich) by reaction with N-maleimidobenzoyl-N-hydroxysuccinimide ester to increase antigenicity.

Rabbits are immunized with the epitope-KLH complex in complete Freund's adjuvant. Immunizations are repeated at intervals thereafter in incomplete Freund's adjuvant. After a minimum of seven weeks for mouse or twelve weeks for rabbit, antisera are drawn and tested for antipeptide activity. Testing involves binding the peptide to plastic, blocking with 1% bovine serum albumin, reacting with rabbit antisera, washing, and reacting with radio-iodinated goat anti-rabbit IgG. Methods well known in the art are used to determine antibody titer and the amount of complex formation.

XIII Purification of Naturally Occurring Protein Using Specific Antibodies

Naturally occurring or recombinant protein is purified by immunoaffinity chromatography using antibodies which specifically bind the protein. An immunoaffinity column is constructed by covalently coupling the antibody to CNBr-activated SEPHAROSE resin (APB). Media containing the protein is passed over the immunoaffinity column, and the column is washed using high ionic strength buffers in the presence of detergent to allow preferential absorbance of the protein. After coupling, the protein is eluted from the column using a buffer of pH 2–3 or a high concentration of urea or thiocyanate ion to disrupt antibody/protein binding, and the protein is collected.

XIV Screening Molecules for Specific Binding Using Polynucleotide or Protein

The polynucleotide, or fragments thereof, or the protein, or portions thereof, are labeled with $^{32}$p-dCTP, Cy3-dCTP, or Cy5-dCTP (APB), or with BIODIPY or FITC (Molecular Probes, Eugene OR), respectively. Libraries of candidate molecules or compounds previously. arranged on a substrate are incubated in the presence of composition, a labeled polynucleotide or protein. After incubation under conditions for either a nucleic acid or amino acid sequence, the substrate is washed, and any position on the substrate retaining label, which indicates specific binding or complex formation, is assayed, and the ligand is identified. Data obtained using different concentrations of the nucleic acid or protein are used to calculate affinity between the labeled nucleic acid or protein and the bound molecule.

XV Two-hybrid Screen

A yeast two-hybrid system, MATCHMAKER LexA Two-Hybrid system (Clontech Laboratories, Palo Alto Calif.), is used to screen for peptides that bind the protein of the invention. A polynucleotide encoding the protein is inserted into the multiple cloning site of a pLexA vector, ligated, and transformed into *E. coli*. cDNA, prepared from mRNA, is inserted into the multiple cloning site of a pB42AD vector, ligated, and transformed into *E. coli* to construct a cDNA library. The pLexA plasmid and pB42AD-cDNA library constructs are isolated from *E. coli* and used in a 2:1 ratio to co-transform competent yeast EGY48[p8op-lacZ] cells using a polyethylene glycol/lithium acetate protocol. Transformed yeast cells are plated on synthetic dropout (SD) media lacking histidine (—His), tryptophan (—Trp), and uracil (—Ura), and incubated at 30C until the colonies have grown up and are counted. The colonies are pooled in a minimal volume of 1×TE (pH 7.5), replated on SD/-His/-Leu/-Trp/-Ura media supplemented with 2% galactose (Gal), 1% raffinose (Raf), and 80 mg/ml 5-bromo-4-chloro-3-indolylβ-d-galactopyranoside (X-Gal), and subsequently examined for growth of blue colonies. Interaction between expressed protein and cDNA fusion proteins activates expression of a LEU2 reporter gene in EGY48 and produces colony growth on media lacking leucine (—Leu). Interaction also activates expression of β-galactosidase from the p8op-lacZ reporter construct that produces blue color in colonies grown on X-Gal.

Positive interactions between expressed protein and cDNA fusion proteins are verified by isolating individual positive colonies and growing them in SD/-Trp/-Ura liquid medium for 1 to 2 days at 30C. A sample of the culture is plated on SD/-Trp/-Ura media and incubated at 30C until colonies appear. The sample is replica-plated on SD/-Trp/-Ura and SD/-His/-Trp/-Ura plates. Colonies that grow on SD containing histidine but not on media lacking histidine have lost the pLexA plasmid. Histidine-requiring colonies are grown on SD/Gal/Raf/X-Gal/-Trp/-Ura, and white colonies are isolated and propagated. The pB42AD-cDNA plasmid, which contains a polynucleotide encoding a protein that physically interacts with the protein, is isolated from the yeast cells and characterized.

All patents and publications mentioned in the specification are incorporated by reference herein. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the field of molecular biology or related fields are intended to be within the scope of the following claims.

What is claimed is:

1. A composition comprising a plurality of polynucleotides having the nucleic acid sequences of SEQ ID NOs:1–11 or the complements thereof.

2. An isolated polynucleotide comprising a nucleic acid sequence of SEQ ID NO:8 or the complement thereof.

3. A composition comprising a polynucleotide of claim 2 and a labeling moiety.

4. A method of using a composition to screen a plurality of molecules to identify at least one ligand which specifically binds a polynucleotide of the composition, the method comprising:

a) combining the composition of claim 1 with a plurality of molecules under conditions to allow specific binding; and b) detecting specific binding; thereby identifying a ligand which specifically binds a polynucleotide.

5. The method of claim 4 wherein the composition is attached to a substrate.

6. The method of claim 4 wherein the molecules to be screened are selected from DNA molecules, RNA molecules, peptide nucleic acids, mimetics, and proteins.

7. A method of using a polynucleotide to purify a ligand, the method comprising:

a) combining the polynucleotide of claim 2 with a sample under conditions to allow specific binding;

b) recovering the bound polynucleotide; and c) separating the ligand from the bound polynucleotide, thereby obtaining purified ligand.

8. The method of claim 7 wherein the polynucleotide is attached to a substrate.

9. A method for using a composition to detect gene expression in a sample, the method comprising:

a) hybridizing the composition of claim 1 to a sample under conditions for formation of one or more hybridization complexes;

b) detecting hybridization complex formation, wherein complex formation indicates gene expression in the sample.

10. The method of claim 9 wherein the polynucleotides of the composition are attached to a substrate.

11. The method of claim 9 wherein the sample is from cartilage, synovium or synovial fluid.

12. The method of claim 9 wherein gene expression indicates the presence of rheumatoid arthritis.

13. A vector comprising a polynucleotide of SEQ ID NO:8.

14. A host cell comprising the vector of claim 13.

15. A method for using a host cell to produce a protein, the method comprising:

a) culturing the host cell of claim 14 under conditions for expression of the protein; and b) recovering the protein from cell culture.

* * * * *

SEQUENCE LISTING

```
<160> NUMBER OF SEQ ID NOS: 17

<210> SEQ ID NO 1
<211> LENGTH: 1298
<212> TYPE: DNA
<213> ORGANISM: Homo sapiens
<220> FEATURE:
<223> OTHER INFORMATION: 402234CB1

<400> SEQUENCE: 1
gggacatgac ttagggaaag tcccaaccgg aatcccccca gcccctgcct gtcaacaccc      60
cccaccctgc aggctggggc cgggctggcg gggccctccc gactgacttc cccttgcaga     120
acccagcggg tgccgcttct ccacccgagg cttccacctc caacgagcca tgttccaggc     180
tgcaggagcc gcccaggcca ccccctctca tgacgccaaa ggcggcggca gcagcacggt     240
gcagcgctcc aagtccttca gcctgcgggc ccaggtgaag gagacctgcg ccgcctgcca     300
gaagaccgtg taccccatgg agcggctggt ggccgacaag ctcatttcc acaactcttg      360 cttctgctgc aagcactgtc acaccaagct cagcctgggc agctacgccg cgctgcacgg     420
ggagttctac tgcaaacccc acttccagca gctgtttaag agcaaaggca actacgacga     480 gggtttggc cgcaagcagc acaaggagct ctgggcccac aaggaggtgg accccggcac      540
caagacggcc tgaggcctct gtaaccttcc accccctctg cggaaggcct ggagccggca     600
gggggaaggt gggaaggagg tcgagctggg cttgcgtggg ggccaggtgg gaaggggatg     660
aggcttgctc aggcgtaggg gaccagggca gggctctgct ccaggactcc ttccttcttc     720
cttctcccgc agccggtgag ggtttggaaa ccaggattgg ggtctgccca ccaccctgct     780
tcctgcttcg ttcagcctcc ctccccacct caccccagga ccccctggga ggcccccaag     840
cccagctccc ctatctaggt gccttttctc cagcaaggag tcagcatgcc cccctcaggg     900
tcccaagctc cctcactgcc accggagact gtgtggcccc cacgtctccc catctacctc     960 taccttaac ctgtttctga gccacggaga cagggaggaa ggagcgcgac agtgccacct     1020
gttgggcatc ataaatgccc ctgcagccca tggggagga gatggggaag tggagccacc     1080
ctgcctctgc agggcaaggc agggcctgcc ccagtggggc ttgggaccat ctcgaaccac     1140
cagcgtggag aagcagaagc aaaagcactc gccaggctgc agcctcaggc actggcaggg     1200
gctggtgcgg ccccactccc ctccccgct cccatttgtg cccatcctgt tgtgaccaac      1260
cccgttttaa acatgtttca atagatccaa aaaaaaaa                             1298
```

<210> SEQ ID NO 2
<211> LENGTH: 532
<212> TYPE: DNA
<213> ORGANISM: Homo sapiens
<220> FEATURE:
<223> OTHER INFORMATION: 569989CB1

<400> SEQUENCE: 2

| | | | | | |
|---|---|---|---|---|---|
| cccacgcgtc | cgccttgaca | ccagcagggt | gacatccgct | attgctactt | ctctgctccc | 60 |
| ccacagttcc | tctggacttc | tctggaccac | agtcctctgc | cagaccctg | ccagacccca | 120 |
| gtccaccatg | atccatctgg | gtcacatcct | cttcctgctt | ttgctcccag | tggctgcagc | 180 |
| tcagacgact | ccaggagaga | gatcatcact | ccctgccttt | taccctggca | cttcaggctc | 240 |
| ttgttccgga | tgtgggtccc | tctctctgcc | gctcctggca | ggcctcgtgg | ctgctgatgc | 300 |
| ggtggcatcg | ctgctcatcg | tgggggcggt | gttcctgtgc | gcacgccac | gccgcagccc | 360 |
| cgcccaagaa | gatggcaaag | tctacatcaa | catgccaggc | aggggctgac | cctcctgcag | 420 |
| cttggacctt | tgacttctga | ccctctcatc | ctggatggtg | tgtggtggca | caggaacccc | 480 |
| cgcccccaact | tttggattgt | aataaaacaa | ttgaaacacc | aaaaaaaaaa | aa | 532 |

<210> SEQ ID NO 3
<211> LENGTH: 1229
<212> TYPE: DNA
<213> ORGANISM: Homo sapiens
<220> FEATURE:
<223> OTHER INFORMATION: 706377CB1

<400> SEQUENCE: 3

| | | | | | |
|---|---|---|---|---|---|
| cagagagccg | cggggaccat | ggagccggtg | ccgctgcagg | acttcgtgcg | cgccttggac | 60 |
| cccgcctccc | tcccgcgcgt | gctgcgggtc | tgctcggggg | tctacttcga | gggctccatc | 120 |
| tatgagatct | ctgggaatga | gtgctgcctc | tccacggggg | acctgatcaa | ggtcacccag | 180 |
| gtccgcctcc | agaaggtggt | ctgtgagaac | ccgaagacca | gccagaccat | ggagctcgcc | 240 |
| cccaacttcc | aggtcttctc | aagtcttagg | attgcagcaa | cacgctcggc | tgcccaaacc | 300 |
| caaggcgaag | accttgccag | agttcatcaa | ggatggctcc | agtacgtaca | gcaagattcc | 360 |
| tgcccacagg | aagggccaca | ggccgctaag | ccccaaaggc | aggatctaga | tgatgatgaa | 420 |
| catgattatg | aagaaatact | tgagcaattt | cagaaaacca | tctaagtgct | ggaggaacca | 480 |
| cgcttcctaa | ctgctgcttc | tcagggaatc | cgacaccagc | caaccatttt | aagcctctaa | 540 |
| aagacctcgg | gcaagtctca | cagaaactga | gctgcagacg | gggagtagct | ttgtggaaac | 600 |
| tgatttgatg | gacactgcac | cagcttcctt | caggttctag | attcttgcta | cttagggcgg | 660 |
| gctggtttgg | acctaacatc | tcgcacgtga | ctccctcagc | ctcagagcct | tgggatgcag | 720 |
| agcagctggc | agggttcctc | tcaatcctgc | aaccccagct | gtcccaccgg | tggatgcaga | 780 |
| ggggaatccg | aggccatcaa | ccttggtgac | agcagcgcag | tgccaatgct | gatcacactg | 840 |
| catgggagat | tttgttaacg | tctgccaccc | ccactctcac | ccccaagctc | taagcccccg | 900 |
| ggaggcctgg | actgtcttcc | tcatctctgt | agcaccaagc | ctgatagatc | tgtatatggt | 960 |
| aaacagggt | ttaaccacat | gtggttaaca | tggattaatg | tgggaacttg | gcttcaagaa | 1020 |
| cacaacctta | ggaccttggg | ccccaaaagc | tggtggtgaa | atgaggagga | gccaatttaa | 1080 |
| gaagaccctt | atgagacct | gaggctgcag | aaactggtag | gtttcatcag | gtggttaaag | 1140 |
| tcgtcaaagt | tgtaagtgac | taaccaagat | tatttcattt | taaaaccata | gaataaaaat | 1200 |
| gacacctgag | cttctctaaa | aaaaaaaa | | | | 1229 |

```
<210> SEQ ID NO 4
<211> LENGTH: 1261
<212> TYPE: DNA
<213> ORGANISM: Homo sapiens
<220> FEATURE:
<223> OTHER INFORMATION: 1221361CB1

<400> SEQUENCE: 4
cggacgcgtg ggcggacgcg tggcggacgc gtgggcggac gcgtgggcgc gatgggcctc      60
ttggaacatt ggtgtgttca tctgcattcg atgtgctgga atccacagga atctgggggt     120
gcacatatcc agggtaaagt cagttaacct cgaccagtgg actcaagaac agattcagtg     180
catgcaagag atgggaaatg gaaaggcaaa ccgactttat gaagcctatc ttcctgagac     240
ctttcggcga cctcagatag acccagctgt tgaaggattt attcgagaca aatatgagaa     300
gaagaaatac atggaccgaa gtctggacat caatgccttt aggaaagaaa agatgacaa      360
gtggaaaaga gggagcgaac cagttccaga aaaaaaattg gaacctgttg ttttttgagaa    420
ggtgaaaatg ccacagaaaa aagaagaccc acagctacct cggaaaagct ccccgaaatc     480
cacagcgcct gtcatggatt tgttgggcct tgatgctcct gtggcctgct ccattgcaaa     540
tagtaagacc agcaataccc tagagaagga tttagatctg ttggcctctg ttccatcccc     600
ttcttcttcg ggttccagaa aggttgtagg ttccatgcca actgcaggga gtgccggctc     660
tgttcctgaa aatctgaacc tgtttccgga gccaggagc aaatcagaag aataggcaa       720
gaaacagctc tctaaagact ccattctttc actgtatgga tcccagacgc tcaaatgcc      780
tactcaagca atgttcatgg ctcccgctca gatggcatat cccacagcct accccagctt     840
ccccgggggtt acacctccta acagcataat ggggagcatg atgcctccac cagtaggcat    900
ggttgctcag ccaggagctt ctgggatggt tgcccccatg gccatgcctg caggctatat    960
gggtggcatg caggcatcaa tgatgggtgt gccgaatgga atgatgacca cccagcaggc  1020
tggctacatg gcaggcatgg cagctatgcc ccagactgtg tatggggtcc agccagctca  1080
gcagctgcaa tggaacctta ctcagatgac ccagcagatg gctgggatga acttctatgg  1140
agccaatggc atgatgaact atggacagtc aatgagtggc ggaaatggac aggcagcaaa  1200
tcagactctc agtcctcaga tgtggaaata aaaacaaaac ccttgtata aaaaaaaaa    1260
a                                                                    1261

<210> SEQ ID NO 5
<211> LENGTH: 1340
<212> TYPE: DNA
<213> ORGANISM: Homo sapiens
<220> FEATURE:
<223> OTHER INFORMATION: 1335016CB1

<400> SEQUENCE: 5
ccctcggaat tcggctcgag cagcaactcg cccctctacc tcgggatcct gtttgcagtg      60
accatgatgg ggccaggcct ggcctttggg ctgggcagcc tcatgctgcg cctttatgtg     120
gacattaacc agatgccaga aggtggtatc agcctgacca taaggacccc cgatgggtg      180
ggtgcctggt ggctgggttt cctcatcgct gccggtgcag tggccctggc tgccatcccc     240
tacttcttct tccccaagga aatgcccaag gaaaaacgtg agcttcagtt tcggcgaaag     300
gtcttagcag tcacagactc acctgccagg aagggcaagg actctccctc taagcagagc     360
cctggggagt ccacgaagaa gcaggatggc ctagtccaga ttgcaccaaa cctgactgtg     420
```

-continued

| | | |
|---|---|---|
| atccagttca ttaaagtctt ccccagggtg ctgctgcaga ccctacgcca ccccatcttc | 480 |
| ctgctggtgg tcctgtccca ggtatgcttg tcatccatgg ctgcgggcat ggccaccttc | 540 |
| ctgcccaagt tcctggagcg ccagttttcc atcacagcct cctacgccaa cctgctcatc | 600 |
| ggctgcctct ccttcccttc ggtcatcgtg ggcatcgtgg tgggtggcgt cctggtcaag | 660 |
| cggctccacc tgggccctgt gggatgcggt gccctttgcc tgctggggat gctgctgtgc | 720 |
| ctcttcttca gcctgccgct cttctttatc ggctgctcca gccaccagat gcgggcatc | 780 |
| acacaccaga ccagtgccca ccctgggctg agctgtctc caagctgcat ggaggcctgc | 840 |
| tcctgcccat tggacggctt aaccctgtc tgcgacccca gcactcgtgt ggaatacatc | 900 |
| acaccctgcc acgcaggctg ctcaagctgg tggtccagg atgctctgga acaacagccag | 960 |
| agtcctccca cctcccaccc tcatgctggg catcagcatc taaacctgag gctcctccag | 1020 |
| ggagagacct gggctgcact ggctggtgca gaagaacctg ttgatggtgc atagtccttc | 1080 |
| agaagccagc caggcaccac ctgggcctga gagcccttcc agagaccccc aggccttggc | 1140 |
| aggtggagca gtgaactcct gtggatatgg gaaccgattc aaatccttct taggcctcta | 1200 |
| actgactctg ttaccttagg caaattattt aactagtgcc tcagtttctt ggtctgtaaa | 1260 |
| atagggagaa tattattaag tgcctactac agagcaggaa tgtgctgaat aaatgctta | 1320 |
| cctggatgaa aaaaaaaaa | 1340 |

<210> SEQ ID NO 6
<211> LENGTH: 2192
<212> TYPE: DNA
<213> ORGANISM: Homo sapiens
<220> FEATURE:
<223> OTHER INFORMATION: 2349263CB1

<400> SEQUENCE: 6

| | | |
|---|---|---|
| ttctttctct atattatgat tactagcact attactgtta ttagttacat gttattgaaa | 60 |
| gcttcaaagc agcataggct ttttataaat attttgctc atctttatga caattctcca | 120 |
| gtgttggtat tgctcctcta tttaacagat tagaaaactg aagcttcaag aacagacttg | 180 |
| cctaacaaca ggaaacttgt atgtctcgaa gtggcaattc acacataagg ctccatgact | 240 |
| cctgaactct cacaaatatt agttggctct tttcatggtt ttactgaagt tgctagaagt | 300 |
| ttacagaaaa ggaagtgcag gaacatttca caaatctaca atctgtgagt atcacatcct | 360 |
| gtatagctgt aaacactgga ataaggaagg gctgatgact ttcagaagat gaaggtaagt | 420 |
| agaaaccgtt gatgggactg agaaaccaga gttaaaacct ctttggagct tctgaggact | 480 |
| cagctggaac caacgggcac agttggcaac accatcatga catcacaacc tgttcccaat | 540 |
| gagaccatca tagtgctccc atcaaatgtc atcaacttct cccaagcaga gaaacccgaa | 600 |
| cccaccaacc aggggcagga tagcctgaag aaacatctac acgcagaaat caaagttatt | 660 |
| gggactatcc agatcttgtg tggcatgatg gtattgagct tggggatcat tttggcatct | 720 |
| gcttccttct ctccaaattt tacccaagtg acttctacac tgttgaactc tgcttaccca | 780 |
| ttcataggac ccttttttt tatcatctct ggctctctat caatcgccac agagaaaagg | 840 |
| ttaaccaagc ttttggtgca tagcagcctg gttggaagca ttctgagtgc tctgtctgcc | 900 |
| ctggtgggtt tcattatcct gtctgtcaaa caggccacct taaatcctgc ctcactgcag | 960 |
| tgtgagttgg acaaaaataa tataccaaca agaagttatg tttcttactt ttatcatgat | 1020 |
| tcactttata ccacggactg ctatacagcc aaagccagtc tggctggaac tctctctctg | 1080 |
| atgctgattt gcactctgct ggaattctgc ctagctgtgc tcactgctgt gctgcggtgg | 1140 |

-continued

```
aaacaggctt actctgactt ccctggggtg agtgtgctgg ccggcttcac ttaaccttgc    1200
ctagtgtatc ttatccctgc actgtgttga gtatgtcacc aagagtggta gaaggaacaa    1260
ccagccaatc acgagataca catgggaggg catttgcatt gtgatggaag acagagaaga    1320
aaagcagatg gcaattgagt agctgataag ctgaaaattc actggatatg aaaatagtta    1380
atcatgagaa atcaactgat tcaatcttcc tattttgtca gcgaagggaa tgagactctg    1440
ggaagttaaa tgactggcct ggcattatgc tatgagtttg tgcctttgct gaggacacta    1500
gaacctggct tgcctccctt ataagcagaa acaatttctg ccacaaccac tagtctcttt    1560
aatagtattg acttggtaaa gggcatttac acacgtaact ggatccagtg aatgtcttat    1620
gctctgcatt tgcccctggt gatcttaaaa ttcgtttgcc tttttaaagc tatattaaaa    1680
atgtattgtt gaatcaaacc cctatggact tattgcttta tttaactgaa ttaaaaagcc    1740
ttgatttatc caaaattgta ttatagagtg tagaatgaat actagggtga taaattgcaa    1800
ttatttgaag aacctggtga tatgctctac ttatcttgga ttagctaaga attctatgta    1860
tacagttgga aaaatggcat atatacatct atcttgaacc tgattgaagt ctgaagacct    1920
aacatatttt gtttcttcta gagtgtactt ttcctgcctc acagttacat tggtaattct    1980
ggcatgtcct caaaaatgac tcatgactgt ggatatgaag aactattgac ttcttaagaa    2040
aaaagggaga atattaatc agaaagttga ttcttatgat aatatggaaa agttaaccat    2100
tatagaaaag caaagcttga gtttcctaaa tgtaagcttt taaagtaatg aacattaaaa    2160
aaaaccatta tttcactgtc aaaaaaaaaa aa                                  2192
```

<210> SEQ ID NO 7
<211> LENGTH: 1992
<212> TYPE: DNA
<213> ORGANISM: Homo sapiens
<220> FEATURE:
<223> OTHER INFORMATION: 2471716CB1

<400> SEQUENCE: 7

```
agaaaactgt gagagagaga atttttaaaa agcagctggg gcctgaggtt tctcccccag      60
taccctgggt cacctcagcc cagagctggc ggcaggcccc cagcccctca tgtcagagcc     120
ccctgtgtac tgtaacctgg tggaccttcg ccgctgtcct cggtccccac ccccaggccc     180
tgcatgcccc ctgctgcaga ggctggatgc ctgggagcag cacctggacc ccaactctgg     240
acgctgcttc tacataaatt cactgactgg ctgcaagtcc tggaagcccc cgcgccgcag     300
tcgcagcgag acgaaccctg ctccatggaa ggggacacag accctgaaga ggaacaatga     360
tgtcctgcaa cctcaggcaa agggcttcag atctgacaca gggaccccag aaccgcttga     420
cccacagggt tcactcagcc tcagccaacg cacctcgcag cttgaccctc cagccttgca     480
ggcccctcga cctctgccgc agctcctgga cgaccccat gaggtggaaa agtcgggtct     540
gctcaacatg accaagattg cccaaggggg cgcaagctc aggaagaact ggggcccgtc     600
ttgggtggtg ttaacgggta acagcctggt gttctaccga gagccaccgc cgacagcgcc     660
ctcctcaggc tggggaccag cgggtagccg gcccgaaagt agcgtggacc tgcgcggggc     720
ggccctggcg cacggccgcc acctgtccag ccgccgcaac gtcctgcaca tccgcacgat     780
ccctggccac gagttcctgc tgcagtcgga ccacgagaca gagctgcgag cctggcaccg     840
cgcgctgcgg actgtcatcg agcggctgga tcgggagaac cccctggagc tgcgtctgtc     900
gggctctgga cccgcggagc tgagcgccgg ggaggacgaa gaagaggagt cggagctggt     960
```

-continued

```
gtccaagccg ctgctgcgcc tcagcagccg ccggagctcc attcggggc ccgaaggcac    1020 cgagcagaac cgcgtgcgca acaaactaaa gcggctcatc gcgaagagac cgcccttaca   1080
aagcctgcag gagcggggtc tgctccgaga ccaggtgttc ggctgccagt tggaatcact   1140
ctgccagcgg gaaggagaca cggtgcccag cttttttgcgg ctctgcattg ctgctgtgga  1200
taaaagaggt ctagatgtgg atggcattta tcgggtgagc gggaacttgg cagtggtcca   1260
gaagcttcgc tttctggtgg acagagagcg tgcggtcacc tccgatggga ggtatgtgtt   1320
cccagaacag ccaggacaag aaggtcggtt agatttggac agtactgagt gggatgacat   1380
tcatgtggtc accggagccc tgaagctttt tctccgggag ctgccccagc tctggtgcc    1440 accactgctg ctgccccatt ccgtgctgc ccttgcactc tccgaatcag agcagtgcct    1500
ctctcagata caagaattaa taggctcaat gccaaagccc aaccatgaca ctctacggta   1560
cctcctggag catttatgca gggtgatagc acactcagat aagaatcgca tgacacccca   1620
caacctggga attgtgtttg gaccaaccct gtttcggcca gagcaggaga catctgaccc   1680
agcagcccat gctctctacc cagggcagct ggtccagctg atgctcacca acttcaccag   1740
cctcttcccc tgatgcaggg aaggaagaag agaaaacata tttccggtca tctctggtgg   1800
tgagaggctg gtgttctgtt ttgaggatat ccctttaaat ctcccaaatg actgtctcta   1860
tcttcatgag tgtgacttga ggtgttggga tgggtgaggg agcttctcta aagaggaaag   1920
tgagtggatt aaccctgct ctcttcttg ttccctgtta tcattcctcc ccgaacataa     1980
taatacataa gt                                                       1992
```

<210> SEQ ID NO 8
<211> LENGTH: 3144
<212> TYPE: DNA
<213> ORGANISM: Homo sapiens
<220> FEATURE:
<223> OTHER INFORMATION: 2726173CB1

<400> SEQUENCE: 8

```
ccttgatgcg ctggcggcct cggccgggaa ctccggggta gatgaccgtg gacagcagca     60
tgagcagtgg gtactgcagc ctggacgagg aactggaaga ctgcttcttc actgctaaga   120
ctaccttttt cagaaatgcg cagagcaaac atctttcaaa gaatgtctgt aaacctgtgg   180
aggagacaca gcgcccgccc acactgcagg agatcaagca gaagatcgac agctacaaca   240
cgcgagagaa gaactgcctg gcatgaaac tgagtgaaga cggcacctac acgggttcca    300
tcaaagtgca tctgaaactc cggcggcctg tgacggtgcc tgctgggatc cggccccagt   360
ccatctatga tgccatcaag gaggtgaacc tggcggctac cacggacaag cggacatcct   420
tctacctgcc cctagatgcc atcaagcagc tgcacatcag cagcaccacc accgtcagtg   480
aggtcatcca ggggctgctc aagaagttca tggttgtgga caatccccag aagtttgcac   540
tttttaagcg gatacacaag gacggacaag tgctcttcca gaaactctcc attgctgacc   600 gcccctcta cctgcgcctg cttgctgggc tgacacgga ggtcctcaac tttgtgctaa     660
aggagaatga aactggagag gtagagtggg atgccttctc catccctgaa cttcagaact   720
tcctaacaat cctggaaaaa gaggagcagg acaaaatcca acaagtgcaa agaagtatg    780 acaagtttag gcagaaactg gaggaggcct aagagaatc ccaggcaaa cctgggtaac     840 cggtcctgct tcctctcctc ctggtgcatt cagatttatt tgtattatta attattattt   900
tgcaacagac acttttcctc aggacatctc tggcaggtgc atttgtgcct gcccagcagt   960
tccagctgtg gcaaaagtct cttccatgga caagtgtttg cacgggggtt cagctgtgcc  1020
```

```
cgcccccagg ctgtgcccca ccacagattc tgccaaggat cagaactcat gtgaaacaaa      1080
cagctgacgt cctctctcga tctgcaagcc tttcaccaac caaatagttg cctctctcgt      1140
caccaaactg gaacctcaca ccagccggca aggaaggaa gaaaggtttt agagctgtgt       1200
gttctttctc tggctttgat tcttctttga gttctcttac ttgccacgta caggaccatt     1260
atttatgagt gaaaagttgt agcacattcc ttttgcaggt ctgagctaag cccttgaaag     1320
cagggtaatg ctcataaaag gactgttccc gcggcccaa ggtgcctgtt gttcacactt      1380
aagggaagtt tataaagcta ctggccccag atgctcaggg taaggagcac caaagctgag     1440
gctggctcag agatctccag agaagctgca gcctgccctg ccctggctc tggccctggc      1500 ccacattgca catggaaacc caaggcata tatctgcgta tgtgtggtac ttagtcacat      1560
ctttgtcaac aaactgttcg tttttaagtt acaaatttga atttaatgtt gtcatcatcg     1620
tcatgtgttt cccaagggg aagccagtca ttgaccattt aaaagtctc ctgctaagta      1680 tggaaatcag acagtaagag aaagccaaaa agcaatgcag agaaaggtgt ccaagctgtc    1740
ttcagccttc cccagctaaa gagcagagga gggcctgggc tacttgggtt ccccatcggc    1800
ctccagcact gcctccctcc tcccactgcg actctgggat ctccaggtgc tgcccaagga    1860
gttgccttga ttacagagag gggagcctcc aattcggcca acttggagtc ctttctgttt    1920
tgaagcatgg gccagacccg gcactgcgct cggagagccg gtgggcctgg cctccccgtc    1980
gacctcagtg ccttttgtt ttcagagaga ataggagta gggcgagttt gcctgaagct      2040
ctgctgctgg cttctcctgc caggaagtga acaatggcgg cggtgtggga gacaaggcca    2100
ggagagcccg cgttcagtat gggttgaggg tcacagacct ccctcccatc tgggtgcctg    2160
agttttgact ccaatcagtg ataccagacc acattgacag ggaggatcaa attcctgact    2220
tacatttgca ctggcttctt gtttaggctg aatcctaaaa taaattagtc aaaaaattcc    2280
aacaagtagc caggactgca gagacactcc agtgcagagg gagaaggact tgtaattttc    2340
aaagcagggc tggttttcca acccagcctc tgagaaacca tttctttgct atcctctgcc    2400
ttcccaagtc cctcttgggt cggttcaagc ccaagcttgt tcgtgtagct tcagaagttc    2460
cctctccgac ccaggctgag tccatactgc ccctgatccc agaaggaatg ctgacccctc    2520
gtcgtatgaa ctgtgcatag tctccagagc ttcaaaggca acacaagctc gcaactctaa    2580 gatttttta aaccacaaaa accctggtta gccatctcat gctcagcctt atcacttccc     2640 tcccttaga aactctctcc ctgctgtata ttaaagggag caggtggaga gtcattttcc    2700
ttcgtcctgc atgtctctaa cattaataga aggcatggct cctgctgcaa ccgctgtgaa    2760
tgctgctgag aacctccctc tatggggatg gctatttat ttttgagaag gaaaaaaaaa    2820
gtcatgtata tatacacata aaggcatata gctatatata aagagataag ggtgtttatg    2880
aaatgagaaa attattggac aattcagact ttactaaagc acagttagac ccaaggccta    2940
tgctgaggtc taaacctctg aaaaaagtat agtatcgagt accccgttccc tcccagaggt    3000 gggagtaact gctggtagtg ccttctttgg ttgtgttgct cagtgtgtaa gtgtttgttt    3060
ccaggatatt ttcttttaa atgtctttct tatatgggtt ttaaaaaaaa gtaataaaag    3120
cctgttgcaa aaatgaaaaa aaaa                                          3144
```

<210> SEQ ID NO 9
<211> LENGTH: 2309
<212> TYPE: DNA
<213> ORGANISM: Homo sapiens
<220> FEATURE:

<223> OTHER INFORMATION: 3054032CB1

<400> SEQUENCE: 9

| | | | | | |
|---|---|---|---|---|---|
| aaggggccca | ggaagatcaa | gttgctgagg | agaaatgggg | aggaagtttt | cctgagtgcc | 60 |
| tatgatgacc | taagtcccct | tctgggacct | aaacccccaa | tctggaaggg | ttcagggagt | 120 |
| ctggagggag | aggcagcagg | atgtggaagg | caggctctgg | acagggtgg | ggaagagcag | 180 |
| gcatgctggg | aagttgggga | ggacaagcag | gctgagcctg | gaggcaggct | agacatcagg | 240 |
| gaagaggcag | agggaagtcc | agagaccaag | gtggaggctg | gaaaggccag | tgaggataga | 300 |
| ggggaggctg | ggggaagcca | agagacaaaa | gtcagattga | gagaagggag | tagggaagag | 360 |
| acagaggcca | aggaagagaa | gtccaaaggt | cagaagaagg | ctgacagtat | ggaggctaaa | 420 |
| ggtgtggagg | aaccaggagg | agatgagtat | acagatgaga | aggaaaaaga | aattgagaga | 480 |
| gaagaggatg | aacaaagaga | ggaagcccag | gtagaagctg | aagggaccct | agagcaaggg | 540 |
| gcccaggaag | atcaagttgc | tgaggagaaa | tgggaagttg | tacagaaaca | agaggctgag | 600 |
| ggagtcagag | aggatgagga | caaaggacag | agggagaagg | ggtaccatga | agcaagaaaa | 660 |
| gaccaaggag | atggtgaaga | cagcagaagc | ccagaagcag | caactgaagg | aggagcaggg | 720 |
| gaggtcagca | aggaacggga | gagtgggggat | ggagaggctg | agggagacca | gagggctgga | 780 |
| gggtactatt | tagaagagga | caccctctct | gaaggttcag | gtgtagcgtc | cctggaggtt | 840 |
| gactgtgcca | agagggcaa | tcctcactct | tctgagatgg | aagaggtagc | cccacagcca | 900 |
| cctcagccag | aggagatgga | gcctgagggg | cagcccagtc | cagacggctg | tctatgcccc | 960 |
| tgttctcttg | gcctgggtgg | cgtgggcatg | cgtctagctt | ccactctggt | tcaggtccaa | 1020 |
| caggtccgct | ctgtgcctgt | ggtgccccc | aagccacagt | ttgccaagat | gcccagtgca | 1080 |
| atgtgtagca | agattcatgt | ggcacctgca | aatccatgcc | cgaggcctgg | ccggcttgat | 1140 |
| gggactcctg | gagaaagggc | ttgggggtcc | cgagcttctc | gatcctcttg | gaggaatggg | 1200 |
| ggtagtcttt | cctttgatgc | tgctgtggcc | ctagcccggg | accgccaaag | gactgaggct | 1260 |
| caaggagttc | ggcgaaccca | gacctgtact | gagggtgggg | attactgcct | catccccaga | 1320 |
| acctcccctt | gtagcatgat | ctctgcccat | tctcctcggc | cccttagctg | cctggagctc | 1380 |
| ccatctgaag | gtgcagaagg | gtctggatcc | cggagtcgtc | ttagtctgcc | ccccagagaa | 1440 |
| ccccaggttc | ctgacccct | gttgtcctct | cagcgcagat | catatgcatt | tgaaacacag | 1500 |
| gctaaccctg | ggaaaggtga | aggactgtga | ttaggaccac | agcccgggc | aaagggacc | 1560 |
| agcaagttgt | cttgaatctc | cagggttcct | gactagctgt | ctcctctgca | gcatgagcag | 1620 |
| ctgtagtgcc | caactctata | ggctttggcc | ctccagcttc | tctctttgac | tgtgggaggc | 1680 |
| actgccttgg | ttggtttacc | tgaacttgtc | tccgacacaa | agcacttatc | tcttaggaga | 1740 |
| ttcccaagaa | agtcaacaag | atcttgttcc | cagggagtgg | gtcattggcc | aaagggaaca | 1800 |
| taaggtaggc | agaaaactta | aaagagtttg | ttaaagtgaa | gactggagaa | attcctccct | 1860 |
| tcctctgagc | tgtgaatctc | tcttcatgaa | agccaaaggt | agagacaggg | aggacagggc | 1920 |
| caggttaggg | ccttccacac | acaaacactt | ctagagttgc | ccattcctgt | tatgttcttg | 1980 |
| gaccctaaga | tacctcctgt | ccctttaaa | tccagattaa | gagaaacgtc | caggaagagc | 2040 |
| tctttgaagc | cctcaatatt | tgttggaggg | actggactcc | tctccagctc | cccaccctct | 2100 |
| gcctccagtc | accatgtgca | agagaggtcc | tgtacagatc | tctctgggct | ctcctttctc | 2160 |
| cttttggaata | acttgttcct | atttcaggaa | agggaaatgg | tgtcactcag | gccctgggac | 2220 |
| tgcttctcca | gccaggctgg | ggccacaggt | cccactctag | tgaaggtcaa | tgtctcagaa | 2280 | taaaagctgt atttttacaa aaaaaaaaa                                           2309

<210> SEQ ID NO 10
<211> LENGTH: 1666
<212> TYPE: DNA
<213> ORGANISM: Homo sapiens
<220> FEATURE:
<223> OTHER INFORMATION: 3055142CB1

<400> SEQUENCE: 10
ctgctcgaga actgaatggc cctgtgcaga gccatagtcc cactgtgggt cctgcaatga      60
gcagggctg ggagtagagg gtttctgggg cctcagggtt ctgggaaagc aacagctatc     120
agagagagaa gggccagacc ccatagcctc ttagattcct ggcagtagaa ggagaaggat     180
gggtaaattg acctctgaag tccctgacca ttagcatggt ctaggatcct ttctagaagg     240
aagatctgag gctctggtgc tcagggggat ggcttgggcc ttttctctca accttggctg     300
agcctacccc ttactttgcc aaagacttga ggaccctgta tgtctggagt tcagtcccct     360
cctctgtggg gctcaggtga ttgaaatgtg gatgaaacat ttctctactt caagaccacc     420
tctccctgca aacaccacac acacatggca tgcatgtacg cacatgcgca cacacacg     480
cacacacctc aataatttct ctcaagtttc ctgagtctcc agaaaaacag cactaacgct     540
ggacctgtct actctcagaa cccggcacag attctctctt gatctccttt tggaatctga     600
gattcttaga agacaggata gggttaaatt tagtagcagc tcagttctag ctaaatcact     660
agaggaagtt aattaacttt aagccttcat ttctccagca ctaaaatgga gtggagagtt     720
ggggtggaaa taagacatcc ttaaaaggtt aaattgtctg caaagcacct agcccagtgc     780
cgagctccca gtaggtgttc agtaaagctt agtgcctgac tttctgaaca ctgattcctc     840
ctgtttggag tcactgggat actctcattg ccgttgggat gttcctcact ccttcccagt     900
tcgtggctga ggcagaaccc agactgaaga gggaagagac attccagagg aggattgcct     960
tcgtcagggt aagggtgggg ctgctcaggg gccctaccct tcaccccctt ctgtatcaga    1020
ttggccctcc cactcccatc tcactctgcg tgtacaatct tccatatccg caagttcact    1080
ggcactcttc tggcacctgg gcaagatccc agaacagagg atggagtgac tggcctcaca    1140
gagcttagtg cccgactcag gggaaatggg actggtgcat gggaaatggt cagcctagga    1200
taggacacga gagtctgaaa ttcaaagcaa ccagcttgaa gtggtttgag aagctggaag    1260
caaacatggg ctagagagat agggcagaag tcaagacgag gatctggact gatgtggaga    1320
aagtagccac ggaagcatga actgtatcct gcacaaagtc cctcttcccc gcctcctaat    1380
tcattatgcc caaaaggcct tacgtgaaat tccagcccag agtactcatg acttgagaga    1440
cgtggacaga gccagcttct accttgcctg gccgtctctc ccctgtctta atgtctgctc    1500
ttgctctaag ctccagaaga gtggcgggcc atgtatcttc aatatgtttt tgctgtatgg    1560
gcaggttgtc ttattatgtg atcaacagat gtccaggaac taatgagtgg aatttaatat    1620
tattgtcaaa taaaacttga tttgtcctat aaaaaaaaaa aaaaa                    1666

<210> SEQ ID NO 11
<211> LENGTH: 1751
<212> TYPE: DNA
<213> ORGANISM: Homo sapiens
<220> FEATURE:
<223> OTHER INFORMATION: 3507924CB1

<400> SEQUENCE: 11

-continued

```
tttagaggtt cctgtttgca tctctgcaac cacttcagaa ggcacgtgtt tggtttgctc        60
tgagcctaac ctagagtgct cgcagcagtc tttcagttga gcttggggac tgcagctgtg       120
gggagatttc agtgcattgc ctccctggg tgctcttcat cttggatttg aaagttgaga        180
gcagcatgtt tgcccactg aaactcatcc tgctgccagt gttactggat tattccttgg       240
gcctgaatga cttgaatgtt tccccgcctg agctaacagt ccatgtgggt gattcagctc       300
tgatgggatg tgttttccag agcacagaag acaaatgtat attcaagata gactggactc       360
tgtcaccagg agagcacgcc aaggacgaat atgtgctata ctattactcc aatctcagtg       420
tgcctattgg gcgcttccag aaccgcgtac acttgatggg ggacatctta tgcaatgatg       480
gctctctcct gctccaagat gtgcaagagg ctgaccaggg aacctatatc tgtgaaatcc       540
gcctcaaagg ggagagccag gtgttcaaga aggcggtggt actgcatgtg cttccagagg       600
agcccaaaga gctcatggtc catgtgggtg gattgattca gatgggatgt gttttccaga       660
gcacagaagt gaaacacgtg accaaggtag aatggatatt tcaggacgg cgcgcaaagg       720
aggagattgt atttcgttac taccacaaac tcaggatgtc tgtggagtac tcccagagct       780
ggggccactt ccagaatcgt gtgaacctgg tgggggacat ttttccgcaat gacggttcca       840
tcatgcttca aggagtgagg gagtcagatg gaggaaacta cacctgcagt atccacctag       900
ggaacctggt gttcaagaaa accattgtgc tgcatgtcag cccggaagag cctcgaacac       960
tggtgaccccc ggcagccctg aggcctctgg tcttggtgg taatcagttg gtgatcattg      1020
tgggaattgt ctgtgccaca atcctgctgc tccctgttct gatattgatc gtgaagaaga      1080
cctgtggaaa taagagttca gtgaattcta cagtcttggt gaagaacacg aagaagacta      1140
atccagagat aaaagaaaaa ccctgccatt ttgaaagatg tgaaggggag aaacacattt      1200
actcccccaat aattgtacgg gaggtgatcg aggaagaaga accaagtgaa aaatcagagg      1260
ccacctacat gaccatgcac ccagtttggc cttctctgag gtcagatcgg aacaactcac      1320
ttgaaaaaaa gtcaggtggg ggaatgccaa aaacacagca agccttttga agaatgga       1380
gagtcccttc atctcagcag cggtggagac tctctcctgt gtgtgtcctg gccactcta      1440
ccagtgattt cagactcccg ctctcccagc tgtcctcctg tctcattgtt tggtcaatac      1500
actgaagatg gagaatttgg agcctggcag agagactgga cagctctgga ggaacaggcc      1560
tgctgagggg aggggagcat ggacttggcc tctggagtgg gacactggcc ctgggaacca      1620
ggctgagctg agtggcctca aaccccccgt tggatcagac cctcctgtgg gcagggttct      1680
tagtggatga gttactggga agaatcagag ataaaaacca acccaaatca ttcctctggc      1740
aaaaaaaaa a                                                            1751
```

<210> SEQ ID NO 12
<211> LENGTH: 127
<212> TYPE: PRT
<213> ORGANISM: Homo sapiens
<220> FEATURE:
<223> OTHER INFORMATION: 402234CD1

<400> SEQUENCE: 12

Met Phe Gln Ala Ala Gly Ala Ala Gln Ala Thr Pro Ser His Asp
 1               5                  10                  15

Ala Lys Gly Gly Gly Ser Ser Thr Val Gln Arg Ser Lys Ser Phe
                20                  25                  30

Ser Leu Arg Ala Gln Val Lys Glu Thr Cys Ala Ala Cys Gln Lys
                35                  40                  45

-continued

```
Thr Val Tyr Pro Met Glu Arg Leu Val Ala Asp Lys Leu Ile Phe
                 50                  55                  60

His Asn Ser Cys Phe Cys Cys Lys His Cys His Thr Lys Leu Ser
             65                  70                  75

Leu Gly Ser Tyr Ala Ala Leu His Gly Glu Phe Tyr Cys Lys Pro
                 80                  85                  90

His Phe Gln Gln Leu Phe Lys Ser Lys Gly Asn Tyr Asp Glu Gly
                 95                 100                 105

Phe Gly Arg Lys Gln His Lys Glu Leu Trp Ala His Lys Glu Val
                110                 115                 120

Asp Pro Gly Thr Lys Thr Ala
                125
```

<210> SEQ ID NO 13
<211> LENGTH: 93
<212> TYPE: PRT
<213> ORGANISM: Homo sapiens
<220> FEATURE:
<223> OTHER INFORMATION: 569989CD1

<400> SEQUENCE: 13

```
Met Ile His Leu Gly His Ile Leu Phe Leu Leu Leu Pro Val
 1               5                  10                  15

Ala Ala Ala Gln Thr Thr Pro Gly Glu Arg Ser Ser Leu Pro Ala
                 20                  25                  30

Phe Tyr Pro Gly Thr Ser Gly Ser Cys Ser Cys Gly Ser Leu
                 35                  40                  45

Ser Leu Pro Leu Leu Ala Gly Leu Val Ala Ala Asp Ala Val Ala
                 50                  55                  60

Ser Leu Leu Ile Val Gly Ala Val Phe Leu Cys Ala Arg Pro Arg
                 65                  70                  75

Arg Ser Pro Ala Gln Glu Asp Gly Lys Val Tyr Ile Asn Met Pro
                 80                  85                  90

Gly Arg Gly
```

<210> SEQ ID NO 14
<211> LENGTH: 225
<212> TYPE: PRT
<213> ORGANISM: Homo sapiens
<220> FEATURE:
<223> OTHER INFORMATION: 2349263CD1

<400> SEQUENCE: 14

```
Met Thr Ser Gln Pro Val Pro Asn Glu Thr Ile Ile Val Leu Pro
 1               5                  10                  15

Ser Asn Val Ile Asn Phe Ser Gln Ala Glu Lys Pro Glu Pro Thr
                 20                  25                  30

Asn Gln Gly Gln Asp Ser Leu Lys Lys His Leu His Ala Glu Ile
                 35                  40                  45

Lys Val Ile Gly Thr Ile Gln Ile Leu Cys Gly Met Met Val Leu
                 50                  55                  60

Ser Leu Gly Ile Ile Leu Ala Ser Ala Ser Phe Ser Pro Asn Phe
                 65                  70                  75

Thr Gln Val Thr Ser Thr Leu Leu Asn Ser Ala Tyr Pro Phe Ile
                 80                  85                  90

Gly Pro Phe Phe Phe Ile Ile Ser Gly Ser Leu Ser Ile Ala Thr
                 95                 100                 105
```

-continued

```
Glu Lys Arg Leu Thr Lys Leu Leu Val His Ser Ser Leu Val Gly
            110                 115                 120

Ser Ile Leu Ser Ala Leu Ser Ala Leu Val Gly Phe Ile Ile Leu
            125                 130                 135

Ser Val Lys Gln Ala Thr Leu Asn Pro Ala Ser Leu Gln Cys Glu
            140                 145                 150

Leu Asp Lys Asn Asn Ile Pro Thr Arg Ser Tyr Val Ser Tyr Phe
            155                 160                 165

Tyr His Asp Ser Leu Tyr Thr Thr Asp Cys Tyr Thr Ala Lys Ala
            170                 175                 180

Ser Leu Ala Gly Thr Leu Ser Leu Met Leu Ile Cys Thr Leu Leu
            185                 190                 195

Glu Phe Cys Leu Ala Val Leu Thr Ala Val Leu Arg Trp Lys Gln
            200                 205                 210

Ala Tyr Ser Asp Phe Pro Gly Val Ser Val Leu Ala Gly Phe Thr
            215                 220                 225

<210> SEQ ID NO 15
<211> LENGTH: 547
<212> TYPE: PRT
<213> ORGANISM: Homo sapiens
<220> FEATURE:
<223> OTHER INFORMATION: 2471716CD1

<400> SEQUENCE: 15

Met Ser Glu Pro Pro Val Tyr Cys Asn Leu Val Asp Leu Arg Arg
  1               5                  10                  15

Cys Pro Arg Ser Pro Pro Gly Pro Ala Cys Pro Leu Leu Gln
             20                  25                  30

Arg Leu Asp Ala Trp Glu Gln His Leu Asp Pro Asn Ser Gly Arg
             35                  40                  45

Cys Phe Tyr Ile Asn Ser Leu Thr Gly Cys Lys Ser Trp Lys Pro
             50                  55                  60

Pro Arg Arg Ser Arg Ser Glu Thr Asn Pro Gly Ser Met Glu Gly
             65                  70                  75

Thr Gln Thr Leu Lys Arg Asn Asn Asp Val Leu Gln Pro Gln Ala
             80                  85                  90

Lys Gly Phe Arg Ser Asp Thr Gly Thr Pro Glu Pro Leu Asp Pro
             95                 100                 105

Gln Gly Ser Leu Ser Leu Ser Gln Arg Thr Ser Gln Leu Asp Pro
            110                 115                 120

Pro Ala Leu Gln Ala Pro Arg Pro Leu Pro Gln Leu Leu Asp Asp
            125                 130                 135

Pro His Glu Val Glu Lys Ser Gly Leu Leu Asn Met Thr Lys Ile
            140                 145                 150

Ala Gln Gly Gly Arg Lys Leu Arg Lys Asn Trp Gly Pro Ser Trp
            155                 160                 165

Val Val Leu Thr Gly Asn Ser Leu Val Phe Tyr Arg Glu Pro Pro
            170                 175                 180

Pro Thr Ala Pro Ser Ser Gly Trp Gly Pro Ala Gly Ser Arg Pro
            185                 190                 195

Glu Ser Ser Val Asp Leu Arg Gly Ala Ala Leu Ala His Gly Arg
            200                 205                 210

His Leu Ser Ser Arg Arg Asn Val Leu His Ile Arg Thr Ile Pro
            215                 220                 225
```

-continued

```
Gly His Glu Phe Leu Leu Gln Ser Asp His Glu Thr Glu Leu Arg
                230                 235                 240

Ala Trp His Arg Ala Leu Arg Thr Val Ile Glu Arg Leu Asp Arg
            245                 250                 255

Glu Asn Pro Leu Glu Leu Arg Leu Ser Gly Ser Gly Pro Ala Glu
        260                 265                 270

Leu Ser Ala Gly Glu Asp Glu Glu Glu Ser Glu Leu Val Ser
    275                 280                 285

Lys Pro Leu Leu Arg Leu Ser Ser Arg Arg Ser Ser Ile Arg Gly
290                 295                 300

Pro Glu Gly Thr Glu Gln Asn Arg Val Arg Asn Lys Leu Lys Arg
                305                 310                 315

Leu Ile Ala Lys Arg Pro Pro Leu Gln Ser Leu Gln Glu Arg Gly
            320                 325                 330

Leu Leu Arg Asp Gln Val Phe Gly Cys Gln Leu Glu Ser Leu Cys
        335                 340                 345

Gln Arg Glu Gly Asp Thr Val Pro Ser Phe Leu Arg Leu Cys Ile
    350                 355                 360

Ala Ala Val Asp Lys Arg Gly Leu Asp Val Asp Gly Ile Tyr Arg
365                 370                 375

Val Ser Gly Asn Leu Ala Val Val Gln Lys Leu Arg Phe Leu Val
                380                 385                 390

Asp Arg Glu Arg Ala Val Thr Ser Asp Gly Arg Tyr Val Phe Pro
            395                 400                 405

Glu Gln Pro Gly Gln Glu Gly Arg Leu Asp Leu Asp Ser Thr Glu
        410                 415                 420

Trp Asp Asp Ile His Val Val Thr Gly Ala Leu Lys Leu Phe Leu
    425                 430                 435

Arg Glu Leu Pro Gln Pro Leu Val Pro Pro Leu Leu Leu Pro His
440                 445                 450

Phe Arg Ala Ala Leu Ala Leu Ser Glu Ser Glu Gln Cys Leu Ser
                455                 460                 465

Gln Ile Gln Glu Leu Ile Gly Ser Met Pro Lys Pro Asn His Asp
            470                 475                 480

Thr Leu Arg Tyr Leu Leu Glu His Leu Cys Arg Val Ile Ala His
        485                 490                 495

Ser Asp Lys Asn Arg Met Thr Pro His Asn Leu Gly Ile Val Phe
    500                 505                 510

Gly Pro Thr Leu Phe Arg Pro Glu Gln Glu Thr Ser Asp Pro Ala
515                 520                 525

Ala His Ala Leu Tyr Pro Gly Gln Leu Val Gln Leu Met Leu Thr
                530                 535                 540

Asn Phe Thr Ser Leu Phe Pro
            545

<210> SEQ ID NO 16
<211> LENGTH: 265
<212> TYPE: PRT
<213> ORGANISM: Homo sapiens
<220> FEATURE:
<223> OTHER INFORMATION: 2726173CD1

<400> SEQUENCE: 16

Met Thr Val Asp Ser Ser Met Ser Ser Gly Tyr Cys Ser Leu Asp
 1               5                  10                  15
```

-continued

Glu Glu Leu Glu Asp Cys Phe Phe Thr Ala Lys Thr Thr Phe Phe
            20                  25                  30

Arg Asn Ala Gln Ser Lys His Leu Ser Lys Asn Val Cys Lys Pro
            35                  40                  45

Val Glu Glu Thr Gln Arg Pro Pro Thr Leu Gln Glu Ile Lys Gln
            50                  55                  60

Lys Ile Asp Ser Tyr Asn Thr Arg Glu Lys Asn Cys Leu Gly Met
            65                  70                  75

Lys Leu Ser Glu Asp Gly Thr Tyr Thr Gly Phe Ile Lys Val His
            80                  85                  90

Leu Lys Leu Arg Arg Pro Val Thr Val Pro Ala Gly Ile Arg Pro
            95                  100                 105

Gln Ser Ile Tyr Asp Ala Ile Lys Glu Val Asn Leu Ala Ala Thr
            110                 115                 120

Thr Asp Lys Arg Thr Ser Phe Tyr Leu Pro Leu Asp Ala Ile Lys
            125                 130                 135

Gln Leu His Ile Ser Ser Thr Thr Val Ser Glu Val Ile Gln
            140                 145                 150

Gly Leu Leu Lys Lys Phe Met Val Val Asp Asn Pro Gln Lys Phe
            155                 160                 165

Ala Leu Phe Lys Arg Ile His Lys Asp Gly Gln Val Leu Phe Gln
            170                 175                 180

Lys Leu Ser Ile Ala Asp Arg Pro Leu Tyr Leu Arg Leu Leu Ala
            185                 190                 195

Gly Pro Asp Thr Glu Val Leu Asn Phe Val Leu Lys Glu Asn Glu
            200                 205                 210

Thr Gly Glu Val Glu Trp Asp Ala Phe Ser Ile Pro Glu Leu Gln
            215                 220                 225

Asn Phe Leu Thr Ile Leu Glu Lys Glu Gln Asp Lys Ile Gln
            230                 235                 240

Gln Val Gln Lys Lys Tyr Asp Lys Phe Arg Gln Lys Leu Glu Glu
            245                 250                 255

Ala Leu Arg Glu Ser Gln Gly Lys Pro Gly
            260                 265

<210> SEQ ID NO 17
<211> LENGTH: 394
<212> TYPE: PRT
<213> ORGANISM: Homo sapiens
<220> FEATURE:
<223> OTHER INFORMATION: 3507924CD1

<400> SEQUENCE: 17

Met Phe Cys Pro Leu Lys Leu Ile Leu Leu Pro Val Leu Leu Asp
 1               5                  10                  15

Tyr Ser Leu Gly Leu Asn Asp Leu Asn Val Ser Pro Glu Leu
            20                  25                  30

Thr Val His Val Gly Asp Ser Ala Leu Met Gly Cys Val Phe Gln
            35                  40                  45

Ser Thr Glu Asp Lys Cys Ile Phe Lys Ile Asp Trp Thr Leu Ser
            50                  55                  60

Pro Gly Glu His Ala Lys Asp Glu Tyr Val Leu Tyr Tyr Tyr Ser
            65                  70                  75

Asn Leu Ser Val Pro Ile Gly Arg Phe Gln Asn Arg Val His Leu
            80                  85                  90

```
                                      -continued

Met Gly Asp Ile Leu Cys Asn Asp Gly Ser Leu Leu Leu Gln Asp
                 95                 100                105

Val Gln Glu Ala Asp Gln Gly Thr Tyr Ile Cys Glu Ile Arg Leu
                110                 115                120

Lys Gly Glu Ser Gln Val Phe Lys Lys Ala Val Val Leu His Val
                125                 130                135

Leu Pro Glu Glu Pro Lys Glu Leu Met Val His Val Gly Gly Leu
                140                 145                150

Ile Gln Met Gly Cys Val Phe Gln Ser Thr Glu Val Lys His Val
                155                 160                165

Thr Lys Val Glu Trp Ile Phe Ser Gly Arg Arg Ala Lys Glu Glu
                170                 175                180

Ile Val Phe Arg Tyr Tyr His Lys Leu Arg Met Ser Val Glu Tyr
                185                 190                195

Ser Gln Ser Trp Gly His Phe Gln Asn Arg Val Asn Leu Val Gly
                200                 205                210

Asp Ile Phe Arg Asn Asp Gly Ser Ile Met Leu Gln Gly Val Arg
                215                 220                225

Glu Ser Asp Gly Gly Asn Tyr Thr Cys Ser Ile His Leu Gly Asn
                230                 235                240

Leu Val Phe Lys Lys Thr Ile Val Leu His Val Ser Pro Glu Glu
                245                 250                255

Pro Arg Thr Leu Val Thr Pro Ala Ala Leu Arg Pro Leu Val Leu
                260                 265                270

Gly Gly Asn Gln Leu Val Ile Ile Val Gly Ile Val Cys Ala Thr
                275                 280                285

Ile Leu Leu Leu Pro Val Leu Ile Leu Ile Val Lys Lys Thr Cys
                290                 295                300

Gly Asn Lys Ser Ser Val Asn Ser Thr Val Leu Val Lys Asn Thr
                305                 310                315

Lys Lys Thr Asn Pro Glu Ile Lys Glu Lys Pro Cys His Phe Glu
                320                 325                330

Arg Cys Glu Gly Glu Lys His Ile Tyr Ser Pro Ile Ile Val Arg
                335                 340                345

Glu Val Ile Glu Glu Glu Pro Ser Glu Lys Ser Glu Ala Thr
                350                 355                360

Tyr Met Thr Met His Pro Val Trp Pro Ser Leu Arg Ser Asp Arg
                365                 370                375

Asn Asn Ser Leu Glu Lys Lys Ser Gly Gly Gly Met Pro Lys Thr
                380                 385                390

Gln Gln Ala Phe
```